(12) United States Patent
Deng et al.

(10) Patent No.: US 11,655,572 B2
(45) Date of Patent: May 23, 2023

(54) METHOD AND APPARATUS FOR RELOFTING A NONWOVEN SUBSTRATE

(71) Applicant: The Procter & Gamble Company, Cincinnati, OH (US)

(72) Inventors: Rong Deng, Mason, OH (US); Aleksey M. Pinyayev, Cincinnati, OH (US); Valerie J. Henderson, Liberty Township, OH (US); Craig A. Powell, Independence, KY (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 621 days.

(21) Appl. No.: 16/690,276

(22) Filed: Nov. 21, 2019

(65) Prior Publication Data

US 2020/0190715 A1 Jun. 18, 2020

Related U.S. Application Data

(60) Provisional application No. 62/780,511, filed on Dec. 17, 2018.

(51) Int. Cl.
  *B29C 35/08* (2006.01)
  *B29C 61/04* (2006.01)
  (Continued)

(52) U.S. Cl.
  CPC ....... *D04H 1/558* (2013.01); *A61F 13/53708* (2013.01); *B29C 61/04* (2013.01);
  (Continued)

(58) Field of Classification Search
  CPC .......... A61F 13/15577; A61F 13/15699; A61F 13/15707; A61F 13/15731; A61F 13/512;
  (Continued)

(56) References Cited

U.S. PATENT DOCUMENTS 3,911,173 A 10/1975 Sprague, Jr.
4,009,814 A 3/1977 Singh
(Continued)

FOREIGN PATENT DOCUMENTS

EP 0538047 A1 4/1993
EP 1403413 B1 4/2008
(Continued)

OTHER PUBLICATIONS

International Search Report and Written Opinion; Application Ser. No. PCT/US2019/066455; dated Apr. 6, 2020; 13 pages.

*Primary Examiner* — Michael A Tolin
(74) *Attorney, Agent, or Firm* — Melissa G. Krasovec; Charles Matson

(57) ABSTRACT

Aspects of the present disclosure relate to methods and apparatuses for relofting nonwoven substrates. During the relofting process, a substrate is directed to advance in a first direction such that a length of the substrate is in a facing relationship with a radiation source. The advancing substrate is relofted by irradiating the length of the substrate with infrared radiation from the infrared radiation source. The substrate comprises a first caliper upstream of the radiation source and the substrate comprises a second caliper downstream of the radiation source greater than the first caliper. The substrate may also be redirected around an axis to advance the substrate in a second direction, wherein the second direction is different than the first direction. The axis may be selectively movable between a first position and a second position to selectively subject the substrate to infrared radiation and remove the substrate from the infrared radiation.

25 Claims, 7 Drawing Sheets

(51) Int. Cl.
*B32B 38/00* (2006.01)
*B32B 3/26* (2006.01)
*D04H 1/558* (2012.01)
*A61F 13/537* (2006.01)
*B32B 5/26* (2006.01)
*D04H 1/485* (2012.01)

(52) U.S. Cl.
CPC ............ *B32B 3/266* (2013.01); *B32B 5/26* (2013.01); *B32B 38/0036* (2013.01); *D04H 1/485* (2013.01); *B29C 2035/0822* (2013.01); *B32B 2038/0088* (2013.01)

(58) Field of Classification Search
CPC ....... A61F 13/53708; A61F 2013/5127; B29C 2035/0822; B29C 61/04; B29L 2031/4878; B32B 3/266; B32B 5/022; B32B 5/26; B32B 38/0036; B32B 2038/0088; B32B 2555/02; D04H 1/06; D04H 1/4382; D04H 1/43825; D04H 1/43828; D04H 1/43832; D04H 1/485; D04H 1/50; D04H 1/541; D04H 1/5412; D04H 1/5414; D04H 1/558; D06C 7/00; D06M 10/001
See application file for complete search history.

(56) References Cited

U.S. PATENT DOCUMENTS

| | | | |
|---|---|---|---|
| 4,157,724 A | 6/1979 | Persson |
| 4,264,289 A | 4/1981 | Day |
| 4,278,113 A | 7/1981 | Persson |
| 4,321,924 A | 3/1982 | Ahr |
| 4,352,649 A | 10/1982 | Jacobsen et al. |
| 4,353,687 A | 10/1982 | Nielsen |
| 4,425,130 A | 1/1984 | Desmarais |
| 4,494,278 A | 1/1985 | Kroyer et al. |
| 4,589,876 A | 5/1986 | Van Tilburg |
| 4,627,806 A | 12/1986 | Johnson |
| 4,650,409 A | 3/1987 | Nistri et al. |
| 4,724,980 A | 2/1988 | Farley |
| 4,785,996 A | 11/1988 | Ziecker et al. |
| 4,842,666 A | 6/1989 | Werenicz |
| 4,940,464 A | 7/1990 | Van Gompel et al. |
| 4,950,264 A | 8/1990 | Osbom, III |
| 5,092,861 A | 3/1992 | Nomura et al. |
| 5,143,779 A | 9/1992 | Newkirk |
| 5,167,897 A | 12/1992 | Weber et al. |
| 5,246,433 A | 9/1993 | Hasse et al. |
| 5,360,420 A | 11/1994 | Cook et al. |
| 5,458,835 A | 10/1995 | Wilkes et al. |
| 5,569,234 A | 10/1996 | Buell et al. |
| 5,599,335 A | 2/1997 | Goldman et al. |
| 5,634,914 A | 6/1997 | Wilkes et al. |
| 5,643,588 A | 7/1997 | Roe et al. |
| 5,674,216 A | 10/1997 | Buell et al. |
| 5,702,551 A | 12/1997 | Huber et al. |
| 5,897,545 A | 4/1999 | Kline et al. |
| 5,957,908 A | 9/1999 | Kline et al. |
| 5,968,025 A | 10/1999 | Roe et al. |
| 6,025,535 A | 2/2000 | Octavio et al. |
| 6,107,356 A | 8/2000 | Desmarais |
| 6,107,537 A | 8/2000 | Elder et al. |
| 6,118,041 A | 9/2000 | Roe et al. |
| 6,120,487 A | 9/2000 | Ashton |
| 6,120,489 A | 9/2000 | Johnson et al. |
| 6,153,209 A | 11/2000 | Vega et al. |
| 6,204,298 B1 | 3/2001 | Desmarais et al. |
| 6,207,724 B1 | 3/2001 | Hird et al. |
| 6,333,108 B1 | 12/2001 | Wilkes et al. |
| 6,410,129 B2 | 6/2002 | Zhang et al. |
| 6,410,820 B1 | 6/2002 | McFall et al. |
| 6,426,444 B2 | 7/2002 | Roe et al. |
| 6,444,716 B1 | 9/2002 | Hird et al. |
| 6,586,652 B1 | 7/2003 | Roe et al. |
| 6,617,016 B2 | 9/2003 | Zhang et al. |
| 6,627,787 B1 | 9/2003 | Roe et al. |
| 6,825,393 B2 | 11/2004 | Roe et al. |
| 6,861,571 B1 | 3/2005 | Roe et al. |
| 7,767,598 B2 | 8/2010 | Schneider et al. |
| 8,211,078 B2 | 7/2012 | Noel |
| 8,702,668 B2 | 4/2014 | Noel |
| 9,237,973 B2 * | 1/2016 | Abuto ............... A61F 13/512 |
| 9,649,228 B2 | 5/2017 | Robles |
| 9,777,414 B2 * | 10/2017 | Okuda ............... D06C 7/00 |
| 2001/0036787 A1 | 11/2001 | Brennan |
| 2003/0233082 A1 | 12/2003 | Kline et al. |
| 2007/0035058 A1 | 2/2007 | Ogle et al. |
| 2008/0312622 A1 | 12/2008 | Hundorf et al. |
| 2013/0072887 A1 | 3/2013 | LaVon et al. |
| 2013/0211356 A1 | 8/2013 | Nishikawa et al. |
| 2013/0306226 A1 | 11/2013 | Zink et al. |
| 2014/0163500 A1 | 6/2014 | Roe et al. |
| 2014/0163506 A1 | 6/2014 | Roe et al. |
| 2014/0163511 A1 | 6/2014 | Roe et al. |
| 2014/0336606 A1 | 11/2014 | Bewick-Sonntag et al. |
| 2014/0343523 A1 | 11/2014 | Viens et al. |
| 2015/0313770 A1 | 11/2015 | Hubbard, Jr. et al. |
| 2015/0335498 A1 | 11/2015 | Hubbard, Jr. et al. |
| 2015/0351976 A1 | 12/2015 | Viens et al. |
| 2015/0374560 A1 | 12/2015 | Hubbard, Jr. |
| 2015/0374561 A1 | 12/2015 | Hubbard, Jr. et al. |
| 2015/0374876 A1 | 12/2015 | Hubbard, Jr. |
| 2016/0129661 A1 | 5/2016 | Arora et al. |
| 2016/0129663 A1 | 5/2016 | Moss et al. |
| 2016/0166443 A1 | 6/2016 | Arora et al. |
| 2016/0167334 A1 | 6/2016 | Arora et al. |
| 2016/0278986 A1 | 9/2016 | Gross et al. |
| 2016/0287452 A1 | 10/2016 | Hubbard, Jr. et al. |
| 2016/0346805 A1 | 12/2016 | McNeil et al. |
| 2016/0375458 A1 | 12/2016 | McNeil et al. |
| 2017/0071795 A1 | 3/2017 | Bewick-Sonntag et al. |
| 2017/0119587 A1 | 5/2017 | Bewick-Sonntag et al. |
| 2017/0119588 A1 | 5/2017 | Bewick-Sonntag et al. |
| 2017/0119589 A1 | 5/2017 | Bewick-Sonntag et al. |
| 2017/0119593 A1 | 5/2017 | Hubbard, Jr. et al. |
| 2017/0119594 A1 | 5/2017 | Bewick-Sonntag et al. |
| 2017/0119595 A1 | 5/2017 | Carla et al. |
| 2017/0119597 A1 | 5/2017 | Bewick-Sonntag et al. |
| 2017/0119598 A1 | 5/2017 | Bewick-Sonntag et al. |
| 2017/0119600 A1 | 5/2017 | Bewick-Sonntag et al. |
| 2017/0258651 A1 | 9/2017 | Hammons et al. |
| 2017/0267827 A1 | 9/2017 | Rowan et al. |
| 2018/0098893 A1 | 4/2018 | Viens et al. |
| 2018/0168884 A1 | 6/2018 | Hubbard, Jr. et al. |
| 2018/0169832 A1 | 6/2018 | Viens et al. |
| 2018/0325753 A1 | 11/2018 | Vohwinkel et al. |

FOREIGN PATENT DOCUMENTS

| | | |
|---|---|---|
| EP | 1447066 | 10/2008 |
| JP | 61-113812 | 5/1986 |
| JP | 2007204876 A * | 8/2007 |
| JP | 2007204876 A | 8/2007 |
| WO | WO 95/11652 | 5/1995 |
| WO | WO 99/00098 | 1/1999 |
| WO | WO 2012/052172 | 4/2012 |

* cited by examiner

METHOD AND APPARATUS FOR RELOFTING A NONWOVEN SUBSTRATE

CROSS REFERENCE TO RELATED APPLICATIONS

This application claims the benefit of U.S. Provisional Application No. 62/780,511, filed on Dec. 17, 2018, the entirety of which is incorporated by reference herein.

FIELD OF THE INVENTION

The present disclosure relates to apparatuses and methods for assembling absorbent articles, and more particularly, methods and apparatuses for relofting nonwoven substrates.

BACKGROUND OF THE INVENTION

Along an assembly line, various types of disposable absorbent articles, such as diapers and sanitary napkins, may be assembled by adding components to and otherwise modifying advancing, continuous webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics. Webs of material and component parts used to manufacture sanitary napkins may include: backsheets, topsheets, secondary topsheets, absorbent core components, release paper wrappers, and the like.

In some configurations, webs of material are supplied on rolls and moved to an absorbent article manufacturing location. During the absorbent article assembly process, webs of material are unwound from the rolls and supplied to an assembly line that converts the webs of material into absorbent articles. In some instances, webs of material may be relatively tightly wound on the rolls, and as such, the associated high winding pressures may compress some types of web materials, such as nonwovens, resulting in a reduced thickness or caliper. Such compressed web materials when incorporated into an absorbent article may have a thin appearance that conveys a message of reduced softness to a consumer and/or may be aesthetically unpleasing.

In order to avoid problems associated with web compression, web materials may be wound less tightly onto rolls in order to reduce the winding pressures. However, less tightly wound web materials may increase roll sizes and/or require reduced quantities of web material that may be wound onto each roll, which may result in increased manufacturing, transportation, and/or storage costs.

In another method to mitigate the problems associated with web compression, some manufacturers may apply heat to the web materials once unwound from the rolls. In turn, the application of heat to some types of web materials may increase the thickness or caliper of the web materials, referred to herein as "relofting". Heat may be applied to the web materials in various ways. However, utilizing heat to reloft webs of materials may present various challenges. For example, some manufactures may apply heat to web materials with hot air. However, hot air systems may require relatively complex design configurations that utilize hot air heaters, fans, ducting, and/or nozzles and may have relatively large space requirements.

In another example, heat may be applied to the web materials with infrared heat sources. Such infrared heat sources may be relatively less complex and relatively smaller than hot air systems. However, infrared heat sources may not start and/or stop quickly, which can create challenges when operating with relatively high speed absorbent article assembly processes. For example, during an assembly line start up, webs of material may be accelerated relatively quickly to high advancement speeds. In some configurations, the webs of material may accelerate to operating speeds more quickly than an infrared source may begin operating at a desired output. As such, it may be important not to introduce an advancing web to heat from the infrared heat source until the heat source is generating the desired heat, otherwise, some portions of the web materials may not be relofted. In another example, during an assembly line shut down, webs of material may be decelerated relatively quickly to zero speed. In some configurations, the webs of material may decelerate to a zero speed more quickly than an infrared source may stop operating at a desired output. As such, it may be important to quickly remove a decelerating or stopped web from heat generated by the infrared heat source. Subjecting a stationary web to continuous heat may result in damage to the web, resulting in increased waste and/or scrap.

Consequently, there remains a need to configure relofting systems to help ensure that substrates treated with the infrared heat sources can operate with substrates that may advance with high acceleration and/or deceleration rates associated with assembly line start ups and shut downs while minimizing unrelofted lengths of substrates and/or without damaging the substrate.

SUMMARY OF THE INVENTION

In one form, a method for relofting a substrate comprises: advancing a substrate in a machine direction MD, the substrate comprising a first surface and an opposing second surface and defining a width in a cross direction; providing a first infrared radiation source; directing a first length of the substrate to advance in a first direction such that the first surface of the first length of the substrate is in a facing relationship with the first radiation source; and irradiating the first surface of the first length of the substrate with infrared radiation from the first infrared radiation source, wherein the substrate comprises a first caliper upstream of the first radiation source and wherein the substrate comprises a second caliper downstream of the first radiation source, wherein the second caliper is at least 1.2 times the first caliper.

In another form, a method making an absorbent article comprises: advancing a substrate in a machine direction MD, the substrate comprising a first surface and an opposing second surface and defining a width in a cross direction; directing the substrate to advance in a first direction; redirecting the substrate around an axis to advance the substrate in a second direction, wherein the second direction is different than the first direction; moving the axis from a first position to a second position to place the first surface of a first length of the substrate in a facing relationship with a first radiation source; and irradiating the first surface of the first length of the substrate with infrared radiation from the first infrared radiation source.

In yet another form, an apparatus for relofting a substrate advancing in a machine direction MD, the substrate comprising a first surface and an opposing second surface and defining a width in a cross direction, comprises: a first infrared radiation source; a second infrared radiation source; an axis adapted to redirect the substrate from a first direction to a second direction, wherein the second direction is different than the first direction; wherein the axis is movable in the first direction from a first position to a second position, wherein when the axis is in the first position, infrared radiation from the first radiation source is not directed toward the first surface of the substrate and infrared radiation from the second radiation source is not directed toward the first surface of the substrate; and wherein when the axis is in the second position, infrared radiation from the first infrared radiation source is directed toward the first surface of the substrate and infrared radiation from the second infrared radiation source is directed toward the first surface of the substrate.

DETAILED DESCRIPTION OF THE INVENTION

Figure 1:
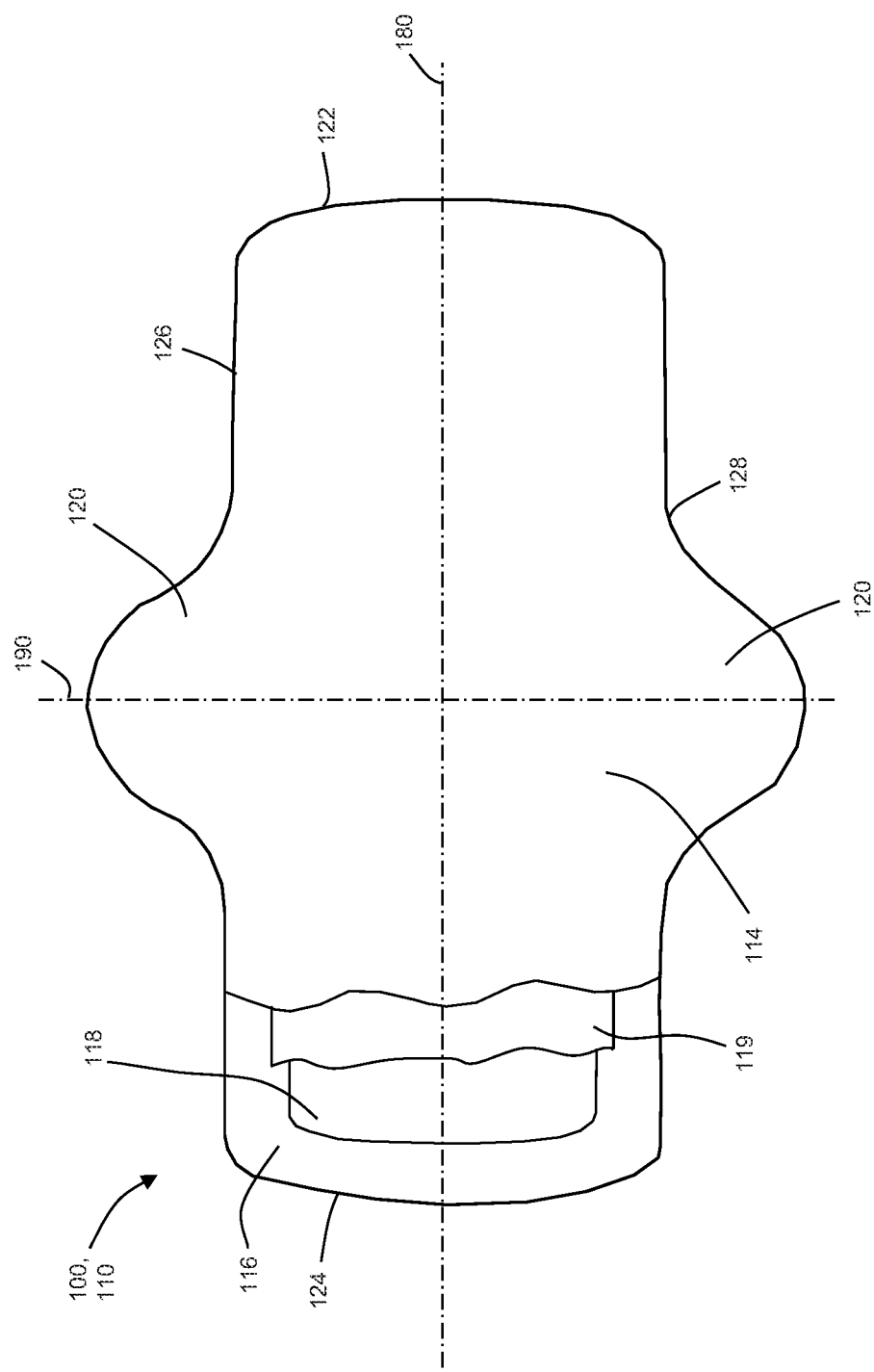
FIG. 1 is a partial cut away plan view of an absorbent article configured as a sanitary napkin.

The following term explanations may be useful in understanding the present disclosure:

"Absorbent article" is used herein to refer to consumer products whose primary function is to absorb and retain soils and wastes. Absorbent articles can comprise sanitary napkins, tampons, panty liners, interlabial devices, wound dressings, wipes, disposable diapers including taped diapers and diaper pants, inserts for diapers with a reusable outer cover, adult incontinent diapers, adult incontinent pads, and adult incontinent pants. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

It is to be appreciated that films having various basis weights can be used in accordance with the methods herein. For example, some films may have a basis weight of at least about 8 gsm, 12 gsm, 16 gsm, 20 gsm, 25 gsm, 25 gsm, 40 gsm, or 60 gsm. Some films may have basis weight of about 8 gsm to about 60 gsm, specifically reciting all 1 gsm increments within the above-recited ranges and all ranges formed therein or thereby.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

Aspects of the present disclosure relate to methods and apparatuses for assembling absorbent articles, and in particular, methods and apparatuses for relofting nonwoven substrates with infrared radiation. During the relofting process, a substrate advances in a machine direction MD, wherein the substrate comprises a first surface and an opposing second surface and defining a width in a cross direction. The substrate is directed to advance in a first direction such that the first surface of a first length of the substrate is in a facing relationship with a radiation source. The advancing substrate is relofted by irradiating the first surface of the first length of the substrate with infrared radiation from the infrared radiation source. In some configurations, the substrate comprises a first caliper upstream of the radiation source and the substrate comprises a second caliper downstream of the radiation source, wherein the second caliper is greater than the first caliper. As discussed in more detail below, the substrate may also be redirected around an axis to advance the substrate in a second direction, wherein the second direction is different than the first direction. The axis may be selectively movable between a first position and a second position to selectively subject the substrate to infrared radiation and remove the substrate from the infrared radiation, such as may be required during assembly line start up and shut down operations.

For example, during assembly line start up operations, the movable axis may be placed in the first position wherein the substrate is isolated from the radiation sources until the radiation sources are generating a desired output of infrared energy. The axis may be moved from the first position to the second position once the radiation sources are operating in a desired manner and/or while the substrate accelerates to a desired advancement speed. Conversely, during assembly line shut down operations, the axis may be moved from the second position to the first position as the radiation sources are shut down but still generating infrared radiation and/or while the substrate decelerates or stops. Thus, the infrared heat sources herein may operate with substrates that may advance with high acceleration and/or deceleration rates associated with assembly line start ups and shut downs while minimizing unrelofted lengths of substrates and/or without damaging the substrate during such assembly line operations.

It is to be appreciated that the systems and methods disclosed herein are applicable to work with various types of converting processes and/or machines, such as for example, absorbent article manufacturing processes. For the purposes of a specific illustration, FIG. 1 shows an example of an absorbent article 100 that may be include components made from substrates that have been relofted in accordance with the methods and apparatuses disclosed herein. In particular, FIG. 1 shows one example of a plan view of an absorbent article 100 configured as a sanitary napkin 110. The sanitary napkin 110 may comprise a liquid permeable topsheet 114, a liquid impermeable, or substantially liquid impermeable, backsheet 116, and an absorbent core 118. The liquid impermeable backsheet 116 may or may not be vapor permeable. The absorbent core 118 may have any or all of the features described herein with respect to the absorbent core 118 and, in some forms, may have a secondary topsheet 119 (STS) instead of acquisition materials. The STS 119 may be positioned between the absorbent core 118 and the topsheet 114. The STS 119 may comprise one or more channels. In some forms, channels in the STS 119 may be aligned with channels in the absorbent core 118. The sanitary napkin 110 may also comprise wings 120 extending outwardly with respect to a longitudinal axis 180 of the sanitary napkin 110. The sanitary napkin 110 may also comprise a lateral axis 190. The wings 120 may be joined to the topsheet 114, the backsheet 116, and/or the absorbent core 118. In some forms, the wings may be provided with zones of extensibility as described in U.S. Pat. No. 5,972,806, which is incorporated by reference herein.

It is to be appreciated that any suitable absorbent core known in the art may be utilized. The absorbent core 118 may be any absorbent member which is generally compressible, conformable, non-irritating to the wearer's skin, and capable of absorbing and retaining liquids such as urine, menses, and/or other body exudates. The absorbent core 118 may be manufactured from a wide variety of liquid-absorbent materials commonly used in disposable absorbent articles such as comminuted wood pulp which is generally referred to as airfelt. The absorbent core 118 may comprise superabsorbent polymers (SAP) and less than 15%, less than 10%, less than 5%, less than 3%, or less than 1% of airfelt, or be completely free of airfelt. Examples of other suitable absorbent materials comprise creped cellulose wadding, meltblown polymers including coform, chemically stiffened, modified or cross-linked cellulosic fibers, tissue including tissue wraps and tissue laminates, absorbent foams, absorbent sponges, superabsorbent polymers, absorbent gelling materials, or any equivalent material or combinations of materials.

The configuration and construction of the absorbent core 118 may vary (e.g., the absorbent core may have varying caliper zones, a hydrophilic gradient, a superabsorbent gradient, or lower average density and lower average basis weight acquisition zones; or may comprise one or more layers or structures). In some forms, the absorbent core 118 may comprise one or more channels, such as two, three, four, five, or six channels.

The absorbent core 118 of the present disclosure may comprise one or more adhesives, for example, to help immobilize the SAP or other absorbent materials within a core wrap and/or to ensure integrity of the core wrap, in particular when the core wrap is made of two or more substrates. The core wrap may extend to a larger area than required for containing the absorbent material(s) within.

Absorbent cores comprising relatively high amounts of SAP with various core designs are disclosed in U.S. Pat. No. 5,599,335; European Patent Publication No. EP 1,447,066; PCT Patent Publication Nos. WO 95/11652 and WO 2012/052172; and U.S. Patent Publication No. 2008/0312622 A1, all of which are incorporated by reference herein. Other forms and more details regarding channels and pockets that are free of, or substantially free of absorbent materials, such as SAP, within absorbent cores are discussed in greater detail in U.S. Patent Publication Nos. 2014/0163500 A1; 2014/0163506 A1; and 2014/0163511 A1, all of which are incorporated by reference herein. Other suitable materials for use in absorbent cores comprise open celled foams or pieces thereof. The use of foams in absorbent cores is described in additional detail in U.S. Pat. Nos. 6,410,820; 6,107,356; 6,204,298; 6,207,724; 6,444,716; 8,211,078; and 8,702,668, all of which are incorporated by reference herein. In some forms, the absorbent core structure may comprise a heterogeneous mass layer or may utilize methods or parameters such as those described in U.S. Patent Publication Nos. 2015/0335498 A1; 2015/0374560 A1; 2015/0374876 A1; 2016/0346805 A1; 2015/0374561 A1; 2016/0287452 A1; 2017/0071795 A1; 2017/0119600 A1; 2017/0119589 A1; 2015/0313770 A1; 2016/0375458 A1; 2017/0119587 A1; 2017/0119597 A1; 2017/0119588 A1; 2017/0119593 A1; 2017/0119594 A1; 2017/0119595 A1; 2017/0119598 A1; 2017/0267827 A1; 2018/0169832 A1; 2018/0169832 A1; 2018/0168884 A1; and 2018/0168884 A1, all of which are incorporated by reference herein.

In some forms, a combination of absorbent core materials may be utilized. For example, forms are contemplated where a first layer of an absorbent core comprises a foam material or pieces thereof as described previously and where a second layer of an absorbent core comprises an airlaid material. Such combinations are described in U.S. Patent Publication No. 2014/0336606 and U.S. Pat. No. 9,649,228, both of which are incorporated by reference herein.

It is to be appreciated that the absorbent core may be formed from various materials, such as multiple plies of creped cellulose wadding, fluffed cellulose fibers, wood pulp fibers also known as airfelt, textile fibers, a blend of fibers, a mass or batt of fibers, airlaid webs of fibers, a web of polymeric fibers, and a blend of polymeric fibers. In some configurations, the absorbent may be made by air-laying the mixture of fibers and thermoplastic material. In general, air-laying can be carried out by metering an airflow containing the fibers and thermoplastic material, in substantially dry condition, onto a typically horizontally moving wire forming screen. Example systems and apparatus for air-laying mixtures of fibers and thermoplastic material are disclosed in, for example in U.S. Pat. Nos. 4,157,724; 4,278,113; 4,264,289; 4,352,649; 4,353,687; 4,494,278; 4,627,806; 4,650,409; and 4,724,980 and U.S. Patent Publication No. 2018/0325753 A1, all of which are incorporated by reference herein.

It is to be appreciated that the secondary topsheet 119 may be made from various materials and formed in various ways, such as discussed for example in U.S. Patent Publication Nos. 2014/0343523 A1; 2015/0351976 A1; and 2018/0098893 A1, all of which are incorporated by reference herein. For example, a secondary topsheet 119 may be made with a spunlace nonwoven. In some forms, the secondary topsheet may comprise superabsorbent similar to the superabsorbent in the absorbent core or different than the absorbent core.

The secondary topsheet 119 can also provide stiffness and flexural rigidity in addition to or in combination with the core which may help prevent, or at least attempt to reduce, cross machine direction (CD) bunching while maintaining comfort and body fit. Accordingly, the secondary topsheet 119 may possess sufficient strength to withstand the swelling of the AGM in the core and the mechanical stresses of user wear, therefore reducing and/or preventing bunching of the absorbent article and providing additional comfort to the user. The secondary topsheet 119 may also be compression resistant and resilient (both dry and wet) to maintain the permeability and capacity of the secondary topsheet and improve acquisition and dryness for the absorbent article while in use.

The secondary topsheet 119 may comprise a carded staple fiber nonwoven and may have a basis weight of 175 grams per square meter (gsm) or less; or a basis weight of 150 gsm or less; or a basis weight in the range of about 30 gsm to about 150 gsm; or in the range of about 45 gsm to about 150 gsm; or in the range of about 45 gsm to about 85 gsm; or in the range of about 55 gsm to about 100 gsm, or in a range of about 50 gsm to about 75 gsm including any values within these ranges and any ranges created thereby. The carded staple fiber nonwoven of the secondary topsheet 119 can also have a cross machine direction (CD) flexural rigidity of about 0.01 mN·cm to about 10 mN·cm. In some embodiments, the carded staple fiber nonwoven has a CD flexural rigidity of about 0.05 mN·cm to about 2 mN·cm or from about 0.07 mN·cm to about 1.0 mN·cm or from about 0.08 mN·cm to about 0.3 mN·cm including any values within these ranges and any ranges created thereby. In some embodiments, the carded staple fiber nonwoven has a MD flexural rigidity of less than about 4.8 mN·cm. In some embodiments, the MD flexural rigidity can be greater than about 0.59 mN·cm. The MD flexural rigidity can be from about 0.60 mN·cm to about 3 mN·cm specifically including all values within this range and all ranges created thereby.

As noted previously, it may be desirable to have stiffness and flexural rigidity in the CD to reduce bunching while maintaining comfort and body fit. For this reason, in some forms, it may be beneficial for the flexural rigidity in the CD to be close to the flexural rigidity of the MD. In some embodiments, the CD flexural rigidity/MD flexural rigidity can be between about 5% to about 32.4% or from about 5.2% to about 7.3%, specifically including all values within these ranges and all ranges created thereby.

The carded staple fiber nonwoven of the secondary topsheet 119 can be manufactured from an assortment of suitable fiber types that produce the desired mechanical performance and fluid handling performance. In some embodiments, the carded staple fiber nonwoven may be formed from a combination of stiffening fibers, absorbing fibers and filler fibers. The stiffening fibers, for example, can form about 10% to about 50%, by weight, of the carded staple fiber nonwoven. For some example secondary topsheets, the stiffening fibers can form about 15% to 35%, by weight, of the carded staple fiber nonwoven. In other embodiments, the stiffening fibers can form about 25%, by weight, of the carded staple fiber nonwoven.

The stiffening fibers can be polyethylene terephthalate (PET) fibers, or other suitable non-cellulosic fibers known in the art. For carded staple fiber nonwovens including PET fibers, the PET fibers can have a dtex in the range of about 3.5 to about 15.0, or in the range of about 6.0 to about 12.0. The staple length of the stiffening fibers can be in the range of about 28 mm to about 100 mm, or in the range of about 37 mm to about 50 mm. Some carded staple fiber nonwovens include stiffening fibers with a staple length of about 38 mm to 42 mm. The PET fibers can have any suitable structure or shape. For example, the PET fibers can be round or have other shapes, such as spiral, scalloped oval, trilobal, scalloped ribbon, and so forth. Further, the PET fibers can be solid, hollow or multi-hollow. In some embodiments of the carded staple fiber nonwoven, the stiffening fibers may be fibers made of hollow/spiral PET. Optionally, the stiffening fibers may be spiral-crimped or flat-crimped. The stiffening fibers may have a crimp value of between about 4 and about 12 crimps per inch (cpi), or between about 4 and about 8 cpi, or between about 5 and about 7 cpi, or between about 9 and about 10 cpi. Particular non-limiting examples of stiffening fibers can be obtained from Wellman, Inc. Ireland under the trade names H1311 and T5974. Other examples of suitable stiffening fibers for utilization in the carded staple fiber nonwovens detailed herein are disclosed in U.S. Pat. No. 7,767,598, which is incorporated by reference herein.

In other embodiments, the stiffening fibers may be bi-component fibers, where individual fibers are provided from different materials, usually a first and a second polymeric material. The two materials may be chemically different (hence the fibers are chemically heterogeneous) or they may differ only in their physical properties while being chemically identical (hence the fibers are chemically homogeneous). For example, may the intrinsic viscosity of the two materials be different, which has been found to influence the crimping behavior of the bi-component fibers. Bi-component fibers that are suitable as stiffening fibers are side-by-side bi-component fibers as disclosed for example in WO 99/00098.

Another suitable bi-component stiffening fiber is a fiber of circular cross section with a hollow space in the centre that is spiral crimped. It is preferred that 10-15% of the cross sectional area are hollow, more preferably 20-30% of the cross sectional area are hollow. Without wishing to be bound by theory, it is believed that the spiral crimping of fibers may be beneficial for their liquid acquisition and distribution behaviour. It is assumed that the spiral crimp increases the void space in an acquisition member formed by such fibers. Often, an absorbent article, when being worn, is exposed to a certain pressure exerted by the wearer, which potentially decreases the void space in the acquisition member. Having good permeability and sufficient void space available may be important for good liquid distribution and transport. The bi-component spiral-crimped fibers as described above may also be suitable to maintain sufficient void volume even when an acquisition member is exposed to pressure. Also, spiral-crimped fibers may help provide for good permeability as for a given fiber dtex value, the hollow fiber cross-section allows for a larger outer diameter of the fiber as compared to a compact cross-section. The outer diameter of a fiber appears to determine the permeability behavior of an acquisition member formed by such fibers.

The absorbing fibers, for example, can form about 10% to about 50%, by weight, of the carded staple fiber nonwoven. For some example secondary topsheets, the absorbing fibers can form about 30% to about 40%, by weight, of the carded staple fiber nonwoven. In other embodiments, the absorbing fibers can form about 35%, by weight, of the carded staple fiber nonwoven.

The absorbing fibers can be rayon, such as viscose rayon, or other suitable cellulosic fibers known in the art, such as cotton (or a blend of these fibers). For carded staple fiber nonwovens including rayon, the rayon can have a dtex in the range of about 1.0 to about 8.0, or from about 2.0 to about 6.0. The staple length of the absorbing fibers can be in the range of about 20 mm to about 100 mm, or about 30 mm to about 50 mm or about 35 mm to about 45 mm. The rayon fibers can have any suitable structure or shape. For example, the rayon fibers can be round or have other shapes, such as spiral, scalloped oval, trilobal, other multi-lobal shapes, scalloped ribbon, and so forth. Further, the rayon fibers can be solid, hollow or multi-hollow. In some embodiments of the carded staple fiber nonwoven, the absorbing fibers may be trilobal in shape, or another shape with a multiple lobes in cross section. Other examples of suitable multi-lobed absorbing fibers for utilization in the carded staple fiber nonwovens detailed herein are disclosed in U.S. Pat. Nos. 6,333,108; 5,634,914; and 5,458,835, all of which are incorporated by reference herein.

Multiple lobed absorbing fibers may provide greater bulk over single-limbed fibers, because the circumferential area of the multiple lobed fibers is larger than their actual cross-sectional area. For example, Japanese Patent Application Kokai 61-113812 describes a filament yarn consisting of X- or Y-shaped continuous viscose filaments that is used in textile applications where bulk is important, for example in pile weaves. Multi-limbed absorbing fibers may provide increased absorbency over single-limbed fibers.

The filler fibers, for example, can form about 1% to about 80%, by weight, of the carded staple fiber nonwoven. For some example secondary topsheets, the filler fibers can form about less than about 60%, by weight, of the carded staple fiber nonwoven. In other embodiments, the filler fibers can form about 40%, by weight, of the carded staple fiber nonwoven.

The filler fibers can be any thermoplastic fiber, such as polypropylene (PP), or other suitable thermoplastic fibers known in the art. For carded staple fiber nonwovens including thermoplastic fibers, the fibers can have a dtex of greater than about 3.0. Some carded staple fiber nonwovens can include PP having a dtex in the range of about 4 to about 10. The staple length of the filler fibers can be in the range of about 20 mm to about 100 mm, or about 30 mm to about 50 mm or about 35 mm to about 45 mm. The thermoplastic fibers can have any suitable structure or shape. For example, the thermoplastic fibers can be round or have other shapes, such as spiral, scalloped oval, trilobal, scalloped ribbon, and so forth. Further, the PP fibers can be solid, hollow or multi-hollow. In some embodiments of the carded staple fiber nonwoven, the third filler fibers may be solid and round in shape. Other suitable examples of filler fibers include bi-component fibers such as polyethylene/polypropylene, polyethylene/polyethylene terephthalate, polypropylene/polyethylene terephthalate. These bi-component fibers may be configured as a sheath and a core.

The carded staple fiber nonwoven of the secondary topsheet 119 may impart a number of physical properties, including narrow pore size distribution, wicking/capillarity, permeability, wet Z-direction crush resistance and flexural rigidity. Generally, the absorbing fibers of the carded staple fiber nonwoven, such as rayon, provide capillarity, which serves to transport fluid from the topsheet 114 to the absorbent core 118. The stiffening fibers of the carded staple fiber nonwoven, such as PET, provide Z-direction strength to prevent, or at least limit, collapse of the secondary topsheet 119 when wetted while also providing desirable permeability. The filler fibers of the carded staple fiber nonwoven, such as polypropylene fibers, serve to provide a cost effective way to increase basis weight of the material while having minimal effect on pore size distribution.

It is to be appreciated that the backsheet 116 may be made from various materials. For example, the backsheet 116 may comprise a liquid impervious film. The backsheet may be impervious to liquids (e.g., body fluids) and may be manufactured from a thin plastic film. The backsheet may permit vapours to escape from the disposable article. In some embodiments, a microporous polyethylene film may be used for the backsheet. An example microporous polyethylene film is manufactured by Mitsui Toatsu Chemicals, Inc., Nagoya, Japan and marketed in the trade as PG-P.

An example material for the backsheet 116 may be a liquid impervious thermoplastic film having a thickness of from about 0.012 mm (0.50 mil) to about 0.051 mm (2.0 mils), for example including polyethylene or polypropylene. In some configurations, the backsheet may have a basis weight of from about 5 g/m$^2$ to about 35 g/m$^2$. However, it should be noted that other flexible liquid impervious materials may be used as the backsheet. Herein, "flexible" refers to materials which are compliant and which will readily conform to the general shape and contours of the wearer's body.

The backsheet 116 may be positioned adjacent an outer-facing surface of the absorbent core and can be joined thereto by any suitable attachment device known in the art. For example, the backsheet may be secured to the absorbent core by a uniform continuous layer of adhesive, a patterned layer of adhesive, or an array of separate lines, spirals, or spots of adhesive. Illustrative, but non-limiting adhesives, include adhesives manufactured by H. B. Fuller Company of St. Paul, Minn., U.S.A., and marketed as HL-1358J. An example of an attachment device including an open pattern network of filaments of adhesive is disclosed in U.S. Pat. No. 4,573,986, which is incorporated by reference herein. Another example attachment device may include several lines of adhesive filaments swirled into a spiral pattern is illustrated by the apparatus and methods shown in U.S. Pat. No. 3,911,173; 4,785,996; and 4,842,666, all of which are incorporated by reference herein. In some configurations, the attachment device may include heat bonds, thermal fusion bonds, pressure bonds, ultrasonic bonds, dynamic mechanical bonds, and/or combinations thereof. The backsheet 116 may be additionally secured to the topsheet 114 by any of the above-cited attachment devices and/or methods.

The topsheet 114 may be positioned adjacent a body-facing surface of the sanitary napkin 110. The topsheet 114 may be joined to the backsheet 116 by attachment methods (not shown) such as those well known in the art. The topsheet 114 and the backsheet 116 may be joined directly to each other in the absorbent article periphery and may be indirectly joined together by directly joining them to the absorbent core 118 by any suitable attachment method.

The topsheet 114 may be compliant, soft feeling, and non-irritating to the wearer's skin. Further, the topsheet 114 may be liquid pervious permitting liquids (e.g., urine, menses) to readily penetrate through its thickness. Some suitable examples of topsheet materials include films, nonwovens, laminate structures including film/nonwoven layers, film/film layers, and nonwoven/nonwoven layers. Additional exemplary topsheet materials and designs are disclosed in U.S. Patent Publication Nos. 2016/0129661 A1, 2016/0167334 A1, 2016/0278986 A1, 2016/0129663 A1, 2016/0166443 A1, and 2017/0258651 A1, all of which are incorporated by reference herein.

The sanitary napkin 110 may also comprise a front edge 122, a back edge 124 longitudinally opposing the front edge 122, a first side edge 126, and a second side edge 128 laterally opposing the first side edge 126. The longitudinal axis 180 may extend from a midpoint of the front edge 122 to a midpoint of the back edge 124. The lateral axis 190 may extend from a midpoint of the first side edge 126 to a midpoint of the second side edge 128. The sanitary napkin 110 may also be provided with additional features commonly found in sanitary napkins as is known in the art.

With regard to the sanitary napkin 110 of FIG. 1, the secondary topsheet 119 incorporating fluid etched stratum of heterogeneous mass may be bonded to, or otherwise attached to the topsheet 114. In some embodiments, thermal point calendaring or other suitable bonding is utilized. In other embodiments, the fluid etched stratum of heterogeneous mass may serve as an absorbent core of an absorbent article. The fluid etched stratum of heterogeneous mass may serve as the topsheet for an absorbent article, the secondary topsheet of an absorbent article. Additionally, an absorbent article may utilize two or more fluid etched stratums of heterogeneous masses within one absorbent article. For example, panty liners and incontinence pads may be formed with the fluid etched stratum of heterogeneous mass positioned between a topsheet and a bottom sheet to function as an absorbent core. Furthermore, the fluid etched absorbent structure having a first layer and a second layer may not include a binder component.

The sanitary napkin 110 may have any shape known in the art for feminine hygiene articles, including the generally symmetric "hourglass" shape, as well as pear shapes, bicycle-seat shapes, trapezoidal shapes, wedge shapes or other shapes that have one end wider than the other.

The topsheet 114, the backsheet 116, and the absorbent core 118 may be assembled in a variety of known configurations, including so called "tube" products or side flap products, such as, for example, configurations are described generally in U.S. Pat. Nos. 4,950,264; 4,425,130; 4,321,924; 4,589,876; and 6,025,535, all of which are incorporated by reference herein.

As previously mentioned, absorbent articles may be assembled with various components that may be relofted off-line, before assembly, or on-line, as part of the assembly process. Thus, in the context of the previous discussion, the apparatuses and methods herein may be used to reloft substrates configured as continuous substrates and/or discrete components of an absorbent article 100, either off-line or on-line. For example, the apparatuses and methods herein may be utilized to reloft any of the topsheet 114; backsheet 116; secondary topsheet 119; and/or absorbent core 118. Although the apparatuses and methods are described herein in the context of the feminine hygiene article 110, such as shown in FIG. 1, it is to be appreciated that the methods and apparatuses herein may be used to reloft various substrates that can be used with various process configurations and/or absorbent articles, such as for example, taped diapers and diaper pants.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1, all of which are incorporated by reference herein.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 5,246,433; 5,569,234; 6,120,487; 6,120,489; 4,940,464; 5,092,861; 5,897,545; 5,957,908; and U.S. Patent Publication No. 2003/0233082 A1, all of which are incorporated by reference herein.

Figure 2:
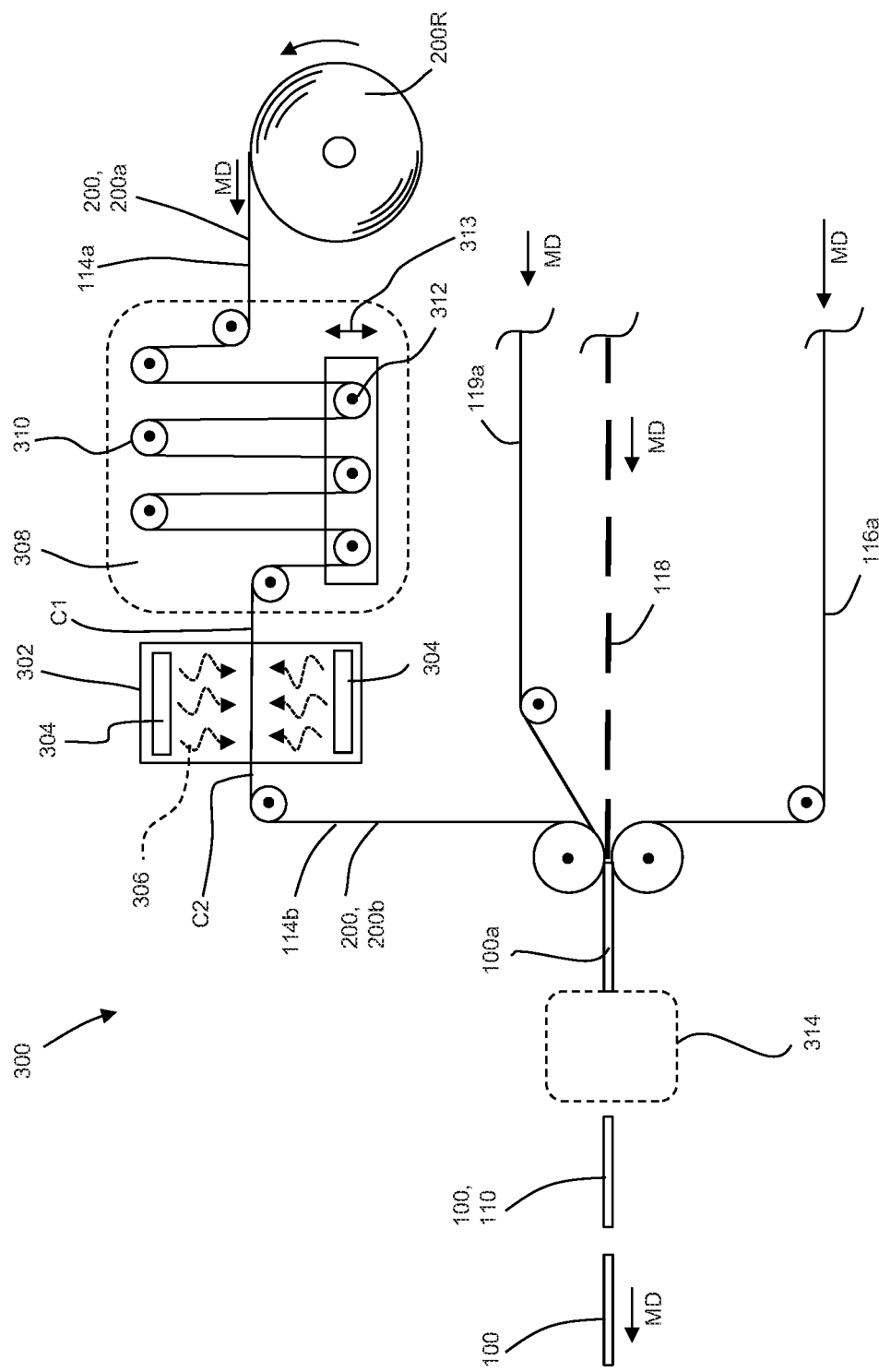
FIG. 2 is a schematic side view of an absorbent article assembly process.

It is to be appreciated that the relofting systems and methods disclosed herein are applicable to work with various types of converting processes and/or machines. For example, FIG. 2 shows a schematic representation of a converting system 300 for assembling absorbent articles 100 that may be configured as sanitary napkins 110. The converting system 300 also includes an apparatus or system 302 for relofting a substrate 200 advancing in a machine direction MD that may be included as a component of the assembled absorbent articles 100.

As shown in FIG. 2, a continuous substrate 200 may be unwound from a roll 200R and advanced in a machine direction MD through a relofting apparatus 302 that applies heat to the advancing substrate 200, which in turn, relofts the substrate 200. More particularly, the substrate 200$a$ upstream of the relofting apparatus 302 comprises a first caliper C1 and the relofted substrate 200$b$ downstream of the relofting apparatus 302 comprises a second caliper C2, wherein the second caliper C2 is greater than the first caliper C1. As discussed in more detail below, the relofting apparatus 302 may include one or more radiation sources 304 that may direct infrared radiation 306 toward the advancing substrate 200, which heats the substrate 200. The relofted substrate 200$b$ may advance from the relofting apparatus 302 to be combined with other advancing substrates and/or components through subsequent converting operations to form assembled absorbent articles 100.

It is to be appreciated that the substrate 200 may be configured in various ways. For example, the substrate may comprise a nonwoven. The term "nonwoven" refers herein to a material made from continuous (long) filaments (fibers) and/or discontinuous (short) filaments (fibers) by processes such as spunbonding, meltblowing, carding, and the like. In some configurations, a nonwoven may comprise a polyolefin based nonwoven, including but not limited to nonwovens having polypropylene fibers and/or polyethylene fibers and/or bicomponent fibers comprising a polyolefin. Nonlimiting examples of suitable fibers include spunbond, spunlaid, meltblown, spunmelt, solvent-spun, electrospun, carded, film fibrillated, melt-film fibrillated, air-laid, dry-laid, wet-laid staple fibers, and other nonwoven web materials formed in part or in whole of polymer fibers as known in the art, and workable combinations thereof Nonwovens may be through-air bonded, such as disclosed in U.S. Patent Publication No. 2001/0036787 A1, which is incorporated herein by reference. Nonwovens do not have a woven or knitted filament pattern. It is to be appreciated that nonwovens having various basis weights can be used in accordance with the methods herein. For example, some nonwovens may have a basis weight of at least about 8 gsm, 12 gsm, 16 gsm, 20 gsm, 25 gsm, 25 gsm, 40 gsm, or 65 gsm. Some nonwovens may have basis weight of about 8 gsm to about 75 gsm, specifically reciting all 1 gsm increments within the above-recited ranges and all ranges formed therein or thereby.

Some nonwovens may comprise PE/PP, PE/PET, PP/PET, PP/PLA, or other bicomponent fiber spunbond webs. Other nonwovens may comprise spunbond webs may comprise side-by-side crimped fibers (for example, PE/PP, PP/PP, PE/PET, PP/PET, PP/PLA,) that are bonded via calendar (thermal point) bonding or through-air bonding. Some nonwovens may comprise carded, through-air bonded or resin bonded (highloft) nonwovens comprising PE/PP or PE/PET fibers. Nonwovens may comprise microfibers and/or nanofibers, and optionally other fibers. In some circumstances, multiple layer nonwovens may be desired over a single layer nonwovens (even at the same basis weight) due to increased uniformity/opacity and the ability to combine webs having different properties. For example, an extensible spunbond nonwoven carrier layer may be combined with a soft, highloft nonwoven (spunbond or carded) to create a laminate nonwoven that is both soft and strong. The layers may have the same or different surface energy. For example, the top layer may be hydrophobic and the lower layer may be hydrophilic. The nonwoven layers may have different permeability/capillarity, for example, the upper layer may have higher permeability and the lower layer have higher capillarity in order to set up a capillary gradient and aid in moving fluid away from the nonwoven's surface or topsheet nonwoven of an absorbent article and into an absorbent core of the absorbent article.

Fibers of the nonwovens may comprise various thermoplastic polymers. Example thermoplastic polymers are polymers that melt and then, upon cooling, crystallize or harden, but that may be re-melted upon further heating. Some thermoplastic polymers may have a melting temperature (also referred to as solidification temperature) from about 60° C. to about 300° C., from about 80° C. to about 250° C., or from about 100° C. to about 215° C., specifically reciting all 0.5° C. increments within the specified ranges and all ranges formed therein or thereby. And, the molecular weight of the thermoplastic polymer may be sufficiently high to enable entanglement between polymer molecules and yet low enough to be melt spinnable.

The thermoplastic polymers may be derived from any suitable material including renewable resources (including bio-based and recycled materials), fossil minerals and oils, and/or biodegradeable materials. Some examples of thermoplastic polymers include polyolefins, polyesters, polyamides, copolymers thereof, and combinations thereof. Some example polyolefins include polyethylene or copolymers thereof, including low density, high density, linear low density, or ultra-low density polyethylenes such that the polyethylene density ranges between about 0.90 grams per cubic centimeter to about 0.97 grams per cubic centimeter or between about 0.92 and about 0.95 grams per cubic centimeter, for example. The density of the polyethylene may be determined by the amount and type of branching and depends on the polymerization technology and co-monomer type. Polypropylene and/or polypropylene copolymers, including atactic polypropylene; isotactic polypropylene, syndiotactic polypropylene, and combination thereof may also be used. Polypropylene copolymers, especially ethylene may be used to lower the melting temperature and improve properties. These polypropylene polymers may be produced using metallocene and Ziegler-Natta catalyst systems. These polypropylene and polyethylene compositions may be combined together to optimize end-use properties. Polybutylene may be a useful polyolefin and may be used in some forms.

Other polymers may include polyamides or copolymers thereof, such as Nylon 6, Nylon 11, Nylon 12, Nylon 46, Nylon 66; polyesters or copolymers thereof, such as maleic anhydride polypropylene copolymer, polyethylene terephthalate; olefin carboxylic acid copolymers such as ethylene/acrylic acid copolymer, ethylene/maleic acid copolymer, ethylene/methacrylic acid copolymer, ethylene/vinyl acetate copolymers or combinations thereof; polyacrylates, polymethacrylates, and their copolymers such as poly(methyl methacrylates).

The thermoplastic polymer component may be a single polymer species or a blend of two or more thermoplastic polymers, for example, two different polypropylene resins. As an example, fibers of a nonwoven or a nonwoven layer may comprise polymers such as polypropylene and blends of polypropylene and polyethylene. In some configurations, a nonwoven or a nonwoven layer may comprise fibers selected from polypropylene, polypropylene/polyethylene blends, and polyethylene/polyethylene terephthalate (PET) blends. In some forms, a nonwoven or a nonwoven layer may comprise fibers selected from cellulose rayon, cotton, other hydrophilic fiber materials, or combinations thereof.

The fibers of a nonwoven or a layer of the nonwoven may comprise monocomponent fibers, bi-component fibers, and/or bi-constituent fibers, round fibers or non-round fibers (e.g., capillary channel fibers), and may have major cross-sectional dimensions (e.g., diameter for round fibers) ranging from about 0.1 microns to about 500 microns. The fibers may also be a mixture of different fiber types, differing in such features as chemistry (e.g. polyethylene, polypropylene, polyester, nylon, etc.), components (mono- and bi-), denier (micro denier and >2 denier), shape (e.g. capillary and round) and the like. The fibers may range from about 0.1 denier to about 100 denier.

Example materials are contemplated where a first plurality of fibers and/or a second plurality of fibers comprise additives in addition to their constituent chemistry. For example, suitable additives include additives for coloration, antistatic properties, lubrication, softness, hydrophilicity, hydrophobicity, and the like, and combinations thereof. These additives, for example titanium dioxide for coloration, may generally be present in an amount less than about 5 weight percent and more typically less than about 2 weight percent or less.

As used herein, the term "monocomponent fiber(s)" refers to a fiber formed from one extruder using one or more polymers. This is not meant to exclude fibers formed from one polymer to which small amounts of additives have been added for coloration, antistatic properties, lubrication, hydrophilicity, etc.

As used herein, the term "bi-component fiber(s)" refers to fibers which have been formed from at least two different polymers extruded from separate extruders but spun together to form one fiber. Bi-component fibers are also sometimes referred to as conjugate fibers or multicomponent fibers. The polymers are arranged in substantially constantly positioned distinct zones across the cross-section of the bi-component fibers and extend continuously along the length of the bi-component fibers. The configuration of such a bi-component fiber may be, for example, a sheath/core arrangement wherein one polymer is surrounded by another, or may be a side-by-side arrangement, a pie arrangement, or an "islands-in-the-sea" arrangement. Some specific examples of fibers which may be used in nonwovens include polyethylene/polypropylene side-by-side bi-component fibers. Another example is a polypropylene/polyethylene bi-component fiber where the polyethylene is configured as a sheath and the polypropylene is configured as a core within the sheath. Still another example is a polypropylene/polypropylene bi-component fiber where two different propylene polymers are configured in a side-by-side configuration. Still yet another example is a polyester (e.g. PET)/polyethylene bi-component fiber where the polyethylene is configured as a sheath and the polyester (e.g. PET)/is configured as a core within the sheath. While still one more example is a polyester (e.g. PET)/ polypropylene bi-component fiber where the polypropylene is configured as a sheath and the polyester (e.g. PET)/is configured as a core within the sheath. Additionally, forms are contemplated where the fibers of a nonwoven are crimped. The crimping may comprise a helical crimp or a kinked crimp.

Bi-component fibers may comprise two different resins, for example, a first polypropylene resin and a second polypropylene resin. The resins may have different melt flow rates, molecular weights, or molecular weight distributions. Ratios of the 2 different polymers may be about 50/50, 60/40, 70/30, 80/20, or any ratio within these ratios. The ratio may be selected to control the amount of crimp, strength of the nonwoven layer, softness, bonding or, the like.

As used herein, the term "bi-constituent fiber(s)" refers to fibers which have been formed from at least two polymers extruded from the same extruder as a blend. Bi-constituent fibers do not have the various polymer components arranged in relatively constantly positioned distinct zones across the cross-sectional area of the fiber and the various polymers are usually not continuous along the entire length of the fiber, instead usually forming fibrils which start and end at random. Bi-constituent fibers are sometimes also referred to as multi-constituent fibers. In some examples, a bi-component fiber may comprise multiconstituent components.

As used herein, the term "non-round fiber(s)" describes fibers having a non-round cross-section, and includes "shaped fibers" and "capillary channel fibers." Such fibers may be solid or hollow, and they may be tri-lobal, delta-shaped, and may be fibers having capillary channels on their outer surfaces. The capillary channels may be of various cross-sectional shapes such as "U-shaped", "H-shaped", "C-shaped" and "V-shaped". One practical capillary channel fiber is T-401, designated as 4DG fiber available from Fiber Innovation Technologies, Johnson City, Tenn. T-401 fiber is a polyethylene terephthalate (PET polyester).

Nonwovens may also comprise aperture spunbond materials, carded materials, melt blown materials, spunlace materials, needle punched materials, wet-laid materials, or air-laid materials. As mentioned herein, the apertured nonwovens may comprise compositions, fiber morphologies, bonding approaches, basis weights, calipers, densities, and other features as described herein. In some configurations, a nonwoven may comprise a carded web of a polyester (PET)/polyethylene bi-component fiber where the polyethylene is configured as a sheath and the polyester (PET)/is configured as a core within the sheath which has been through-air bonded and has a basis weight within the range of 12 to 150 gsm, specifically reciting all 1 gsm increments within the above-recited ranges and all ranges formed therein or thereby.

It is to be appreciated that the systems 300 herein may be configured to advance the substrate 200 through the relofting apparatus 302 at various speeds. For example, in some configurations, the substrate 200 may advance through the relofting apparatus 302 at speeds ranging from about 1 meter per second (m/s) to about 9 meters per second (m/s), specifically reciting all 0.1 meter per second increments within the above-recited range and all ranges formed therein or thereby. As shown in FIG. 2, the system 300 may also include an accumulator 308 to help maintain desired tensions and/or advancement speeds of the advancing substrate 200. It is to be appreciated that the accumulator 308 may be configured in various ways. For example, as shown in FIG. 2, the accumulator 308 may include various configurations of stationary rollers 310 and movable rollers 312. In some configurations, the movable rollers 312 may be adapted to move in directions represented by bi-directional arrow 313. Other examples of accumulator configurations are disclosed in U.S. Pat. Nos. 4,009,814 and 5,163,359, both of which are incorporated by reference herein. Methods of accumulation may also be accomplished by programming a controller to drive various rollers and/or material unwinders at variable angular velocities to help maintain desired tensions and/or advancement speeds of the advancing substrate 200.

As previously discussed, the relofting systems 302 include one or more radiation sources 304 to heat the advancing substrate 200. More particularly, the one or more radiation sources 304 are configured to irradiate and/or direct infrared radiation 306 toward the advancing substrate 200, which in turn, heats the substrate 200. The term "infrared radiation" refers herein to electromagnetic radiation having wavelengths of about 700 nanometers (nm) to about 1 millimeter (mm). In some configurations, the radiation source may be configured to generate infrared radiation 306 that comprises a wavelength that is about equal to a peak absorbance wavelength of the substrate 200. The peak absorbance wavelength for a particular substrate may be measured according to the Peak Absorbance Wavelength Test Method described herein. For example, in some configurations, the wavelength of the infrared radiation 306 and/or the peak absorbance wavelength may range from about 2000 nm to about 4000 nm, specifically reciting all 1 nm increments within the above-recited ranges and all ranges formed therein or thereby. It is to be appreciated that the radiation sources 304 herein may be configured in various ways, such as for example, infrared electric heaters available from Solar Products, Inc. The radiation sources 304 may be configured to operate with various levels of intensity. For example, the radiation sources 304 may be configured to operate such that the intensity of the infrared radiation 306 is from about 5 Watts/inch$^2$ to about 10 Watts/inch$^2$, specifically reciting all 0.5 Watts/inch$^2$ increments within the above-recited ranges and all ranges formed therein or thereby. In another example, the radiation sources 304 may be configured to operate such that the intensity of the infrared radiation 306 is from about 2 Watts/inch$^2$ to about 12 Watts/inch$^2$, specifically reciting all 0.5 Watts/inch$^2$ increments within the above-recited ranges and all ranges formed therein or thereby. It is also to be appreciated that system 300 herein may be configured to irradiate lengths of the advancing substrate 200 to infrared radiation 306 for various lengths of time. For example, in some configurations, the system 300 may be configured to irradiate lengths of the advancing substrate 200 with infrared radiation 306 for about 0.25 second to about 0.75 seconds, specifically reciting all 0.05 second increments within the above-recited ranges and all ranges formed therein or thereby. In yet another example, the radiation sources 304 may be configured to operate such that the intensity of the infrared radiation 306 is from about 2 Watts/inch$^2$ to about 50 Watts/inch$^2$, specifically reciting all 0.5 Watts/inch$^2$ increments within the above-recited ranges and all ranges formed therein or thereby. It is to be appreciated that "intensity" referred to herein may be characterized as nominal power density, which may be calculated as the total electrical power of the radiation source divided by the heated area.

It is also to be appreciated that the substrate may comprise various levels of average absorbance. For example, in some configurations, the substrate may comprise an average absorbance from about 40% to about 70%, specifically reciting all 1% increments within the above-recited ranges and all ranges formed therein or thereby. In some configurations, the substrate may comprise an average absorbance from about 10% to about 90%, specifically reciting all 1% increments within the above-recited ranges and all ranges formed therein or thereby. The average absorbance of a particular substrate can be calculated utilizing data obtained from measurements taken with the Peak Absorbance Wavelength Test Method described herein.

It is to be appreciated that the relofting systems 302 herein may be configured to heat the advancing substrate 200 to various temperatures and may reloft the substrate 200 to increase the caliper of the substrate by various amounts. For example, in some configurations, the relofting system 302 may heat the advancing substrate 200 to temperatures ranging from about 70° C. to about 110° C., specifically reciting all 0.1° C. increments within the above-recited range and all ranges formed therein or thereby.

As discussed above, the substrate 200 may comprise a first caliper C1 upstream of and/or before being heated by the at least one radiation source 304. In addition, the substrate 200 may comprise a second caliper C2 downstream of and/or after being heated by the at least one radiation source 304, wherein the second caliper C2 is greater than the first caliper C1. The caliper of a particular substrate may be measured according to the Caliper Test Method described herein. In some configurations, the second caliper C2 may be at least about 1.2 times the first caliper C1. In some configurations, the second caliper C2 may be from about 1.2 times the first caliper C1 to about 3 times the first caliper C2. In some configurations, the first caliper C1 may range from about 0.25 mm to about 0.45 mm, and the second caliper C2 may range from about 0.40 mm to about 1.0 mm, specifically reciting all 0.05 mm increments within the above-recited ranges for C1 and C2 and all ranges formed therein or thereby. In some configurations, the first caliper C1 may range from about 0.40 mm to about 0.80 mm, and the second caliper C2 may range from about 0.80 mm to about 1.50 mm, specifically reciting all 0.05 mm increments within the above-recited ranges for C1 and C2 and all ranges formed therein or thereby. In some configurations, the first caliper C1 may range from about 1.00 mm to about 1.80 mm, and the second caliper C2 may range from about 1.40 mm to about 2.00 mm, specifically reciting all 0.05 mm increments within the above-recited ranges for C1 and C2 and all ranges formed therein or thereby.

In some configurations, the substrate 200 may comprise apertures, and such apertures may be arranged to define a pattern. The relofting processes herein may also operate to change the aspect ratios of the apertures in the substrate 200. The aspect ratios of apertures in a particular substrate may be measured according to the Aspect Ratio Test Method described herein. In some configurations, apertures in the substrate 200 upstream of and/or before being heated by the at least one radiation source 304 may comprise first aspect ratios, and the apertures downstream of and/or after being heated by the at least one radiation source 304 may comprise second aspect ratios, wherein the second aspect ratios are greater than the first aspect ratios. For example, apertures in the substrate 200 upstream of and/or before being heated by the at least one radiation source 304 may comprise first aspect ratios of about 1 to about 2. And apertures downstream of and/or after being heated by the at least one radiation source 304 may comprise second aspect ratios of about 1.5 to about 4.

Referring again to FIG. 2, the substrate 200 may be configured as a continuous topsheet substrate 114. As such, the continuous topsheet substrate 114a may be unwound from the roll 200R and may advance in the machine direction MD through an accumulator 308. As discussed above, the accumulator 308 may be configured to adjust and/or the tension and/or speed of the advancing topsheet substrate 114a. From the accumulator 308, the continuous topsheet substrate 114a advances through a relofting system 302 that heats and relofts the topsheet substrate 114a. The relofted topsheet substrate 114b advances from the relofting system 302 to downstream converting operations, wherein the relofted topsheet substrate 114b may be combined with other substrates and components such as a secondary topsheet substrate 119a, absorbent cores 118, and a backsheet substrate 116a to form a continuous length of absorbent articles 100a. In some configurations, the secondary topsheet substrate 119a may be separated into discrete pieces before being combined with the relofted topsheet substrate 114b, absorbent cores 118, and backsheet substrate 116a. As shown in FIG. 2, the continuous length of absorbent articles 100a may advance to a cutter apparatus 314 that separates the continuous length of absorbent articles 100a into discrete absorbent articles 100, such as the sanitary napkin 110 shown for example in FIG. 1. The cutter apparatus 314 is generically represented by dashed rectangle in FIG. 2. It is to be appreciated that the cutter apparatus 314 may be configured in various ways, such as for example, a knife roll and an anvil roll.

Figure 3:
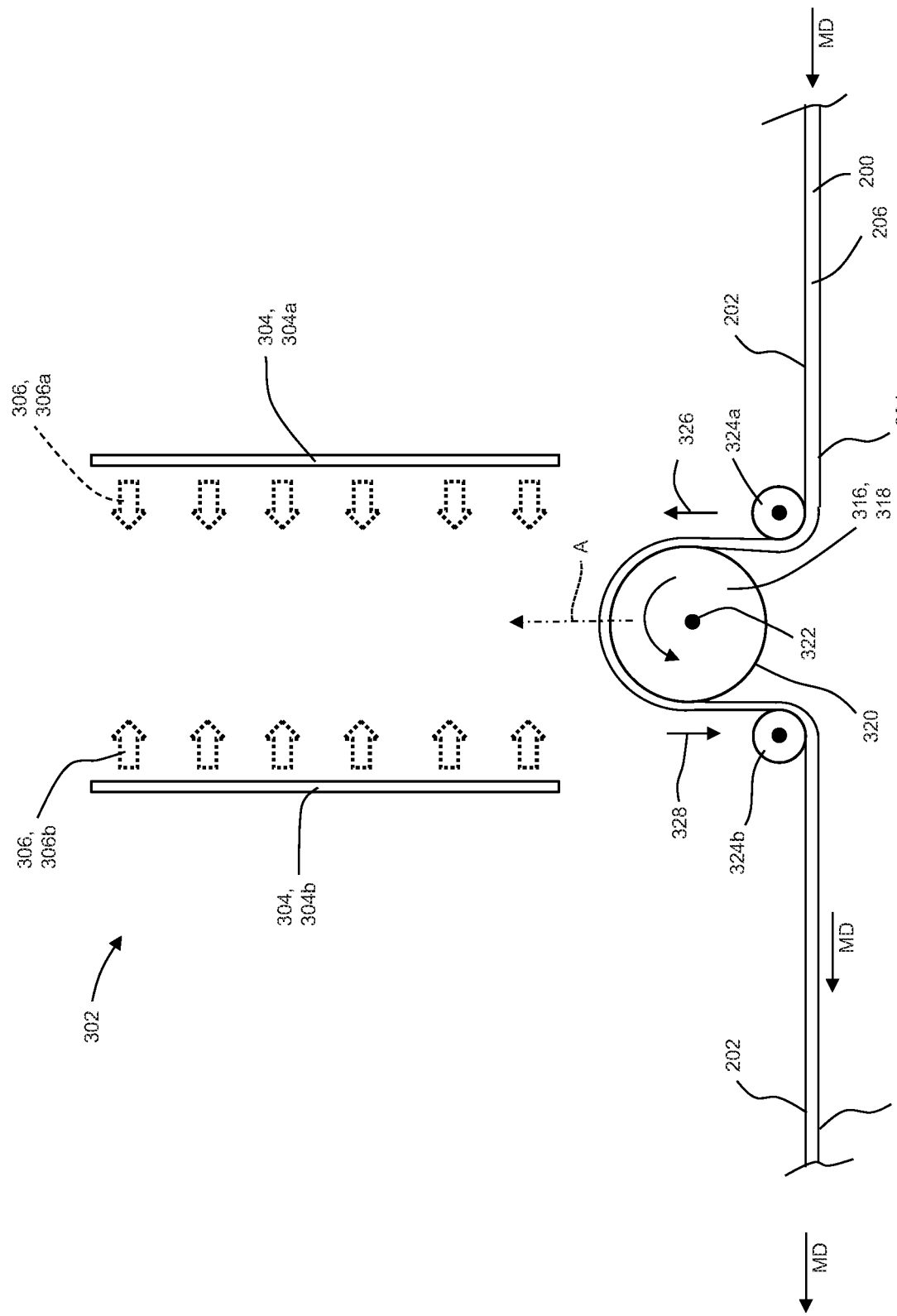
FIG. 3 is a schematic side view of a system for relofting an advancing substrate with a movable axis in a first position.
Figure 4:
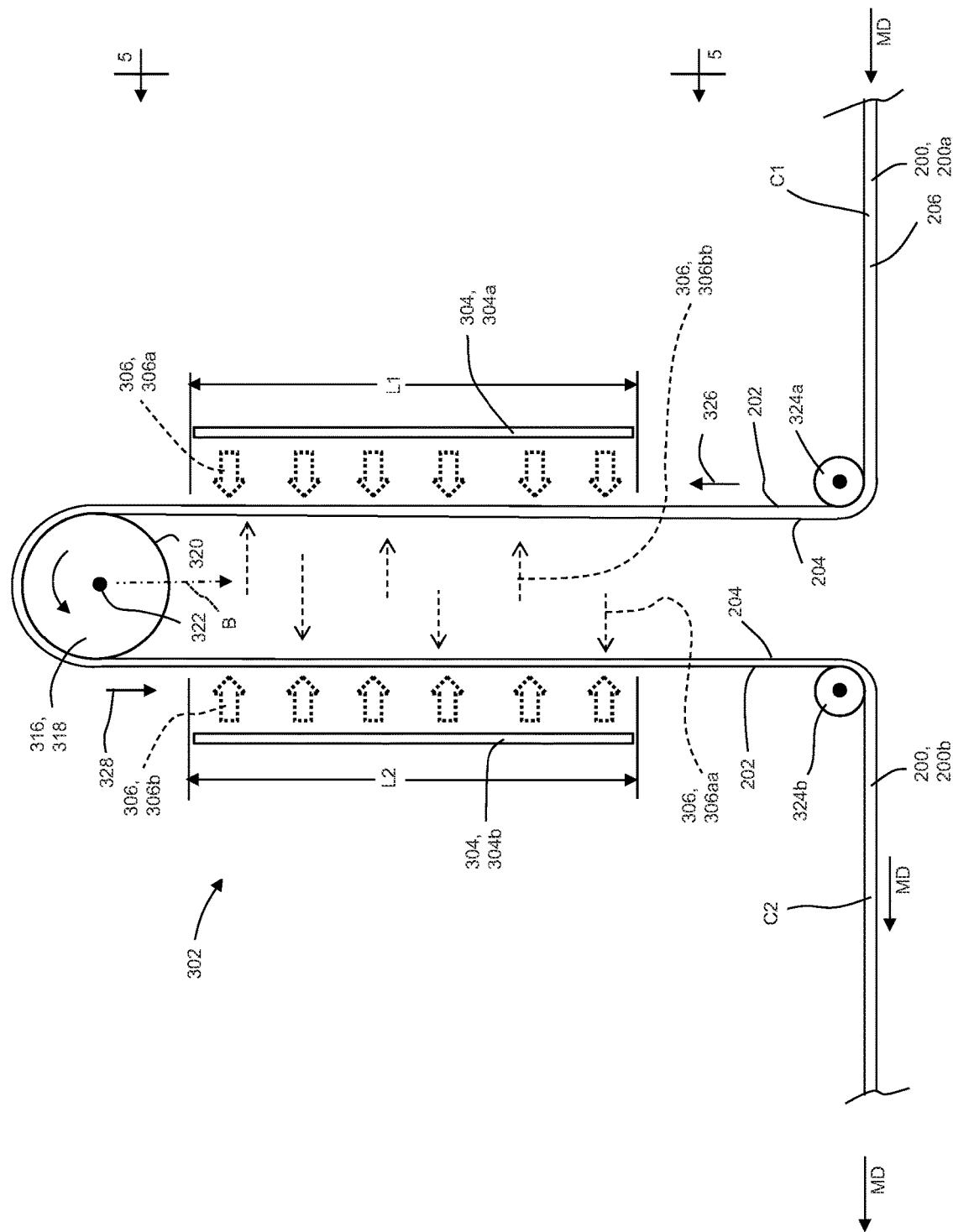
FIG. 4 is a schematic side view of the system of FIG. 3 with the movable axis in a second position.

It is to be appreciated that the relofting systems 302 herein may be configured in various ways. For example, FIGS. 3 and 4 show a relofting system 302 including a movable axis 316. As discussed in more detail below, the movable axis 316 may be configured to move so as to subject the substrate 200 to infrared radiation 306, such as may be required during start up of the assembly line 300. In addition, the movable axis 316 may be configured to move so as to remove the substrate 200 from infrared radiation 306, such as may be required during shut down of the assembly line 300.

Figure 5:
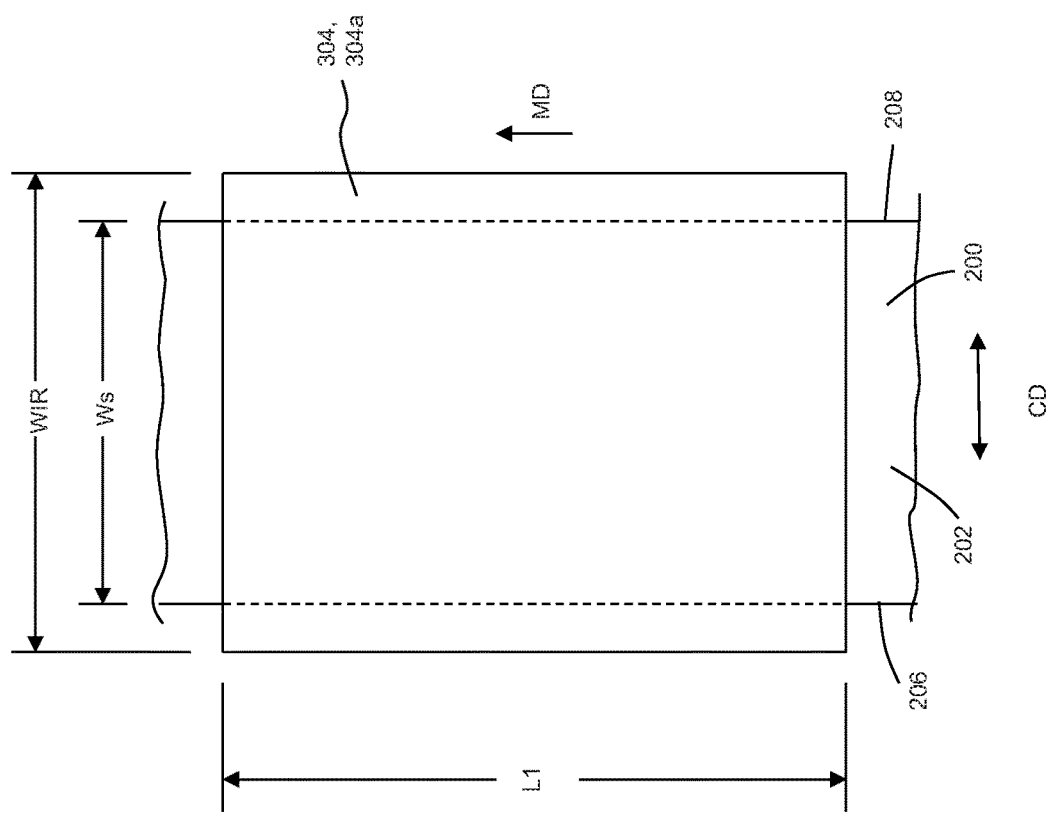
FIG. 5 is a side view of the advancing substrate taken along the sectional line 5-5 of FIG. 4.

As shown in FIGS. 3-5, the relofting system 302 includes a movable axis 316 that may be configured as a traversing idler 318 including an outer circumferential surface 320 adapted to rotate about an axis of rotation 322. The substrate 200 may be a continuous substrate and may include a first surface 202 and an opposing second surface 204. The substrate 200 may also define a width Ws extending in the cross direction CD between a first longitudinal side edge 206 and a second longitudinal side edge 208. As previously mentioned, the relofting apparatus 302 may include one or more radiation sources 304. For example, as shown in FIGS. 3-5, the relofting system 302 may include a first radiation source 304a and a second radiation source 304b, both of which are configured to produce infrared radiation 306. The radiation sources 304 may define a width WIR in the cross direction CD. In some configurations, the width WIR radiation sources 304 may be greater than or equal to the width Ws of the substrate 200. It is also to be appreciated that the radiation sources 304 may each comprise one or more individual infrared heaters.

In operation, a first guide roller 324a may direct the advancing substrate 200 in a first direction 326 to the traversing idler 318. The second surface 204 of the substrate 200 may wrap partially around the outer circumferential surface 320 of the traversing idler 318. As such, the traversing idler 318 may redirect the substrate 200 in a second direction 328 that is different from the first direction 326. As shown in FIGS. 3 and 4, the second direction 328 may be opposite the first direction 326. The substrate 200 may advance from the traversing idler 318 to a second guide roller 324b that may direct the substrate 200 to other downstream converting and/or assembly operations. It is to be appreciated that the relofting system 302 may include more or less guide rollers than depicted in FIGS. 3 and 4.

As previously mentioned, the movable axis 316 may be movable from a first position to a second position to place the substrate 200 in position so as to be heated by the radiation sources 304, such as during assembly line start up operations. For example, FIG. 3 illustrates the movable axis 316 in the first position. As shown in FIG. 3, when the movable axis 316 is in the first position, infrared radiation 306a generated by the first radiation source 304a and infrared radiation 306b generated by the second radiation source 304b is not directed toward the substrate 200. As such, the substrate 200 may be isolated from and may not be heated by the infrared radiation 306 when the movable axis 316 is in the first position.

The movable axis 316 may be configured to move in a direction A from the first position shown in FIG. 3 to a second position shown in FIG. 4. In some configurations, such movement from the first position to the second position may occur once the radiation sources 304 are generating a desired energy output and/or the substrate 200 is accelerating to a desired speed. Movement of the movable axis 316 from the first position to the second position may operate to place the first surface 202 of the substrate 200 in a facing relationship with a radiation source 304.

As shown in FIG. 4, when the movable axis 316 is in the second position, a first length L1 of the first surface 202 of the substrate 200 is in a facing relationship with the first radiation source 304a, and a second length L2 of the first surface 202 of the substrate 200 is in a facing relationship with the second radiation source 304b. The first length L1 of the substrate 200 may advance in the first direction 326 past the first radiation source 304a, and the second length L2 of the substrate 200 may advance in the second direction 328 past the second radiation source 304b. As such, the first radiation source 304a irradiates the first length L1 of the first surface 202 of the advancing substrate 200 with infrared radiation 306a. And the second radiation source 304b irradiates the second length L2 of the first surface 202 of the advancing substrate 200 with infrared radiation 306b. In turn, infrared radiation 306 heats the advancing substrate 200 when the movable axis 316 is in the second position. As shown in FIG. 4, the substrate 200a upstream of the relofting apparatus 302 comprises a first caliper C1, and the infrared radiation 306 heats the substrate such that the caliper of the substrate 200b downstream increases to a second caliper C2 that is greater than the first caliper C1.

In some configurations, some infrared radiation 306 may travel through the substrate 200, and such infrared radiation 306 may be utilized to irradiate other portions of the substrate 200. For example, as shown in FIG. 4, the movable axis 316 may redirect the second length L2 of the substrate 200 from the first direction 326 to advance in the second direction 328 such that the second surface 204 of the first length L1 of the substrate 200 is in a facing relationship with the second surface 204 of the second length L2 of the substrate 200. In turn, a portion 306aa of the infrared radiation 306a from the first radiation source 304a may travel through the first length L1 of the substrate 200 and away from the second surface 204 of the first length L1 of the substrate 200 and may irradiate the second surface 204 of the second length L2 of the substrate 200. In addition, a portion 306bb of the infrared radiation 306b from the second radiation source 304b may travel through the second length L2 of the substrate 200 and away from the second surface 204 of the second length L2 of the substrate 200 and may irradiate the second surface 204 of the first length L2 of the substrate 200.

In some configurations, the relofting system 302 may include one or more mirrors to reflect infrared radiation 306 toward the substrate 200. For example, with reference to FIG. 4, some of the portion 306aa of the infrared radiation 306a from the first radiation source 304a that travels through the first length L1 of the substrate 200 and away from the second surface 204 of the first length L1 of the substrate 200 may also travel through the second length L2 of the substrate 200 and away from the first surface 202 of the second length L2 of the substrate 200. As such, the second radiation source 304b may be configured as or to include a mirror that reflects the portion 306aa of the infrared radiation 306a back toward the first surface 202 of the second length L2 of the substrate 200 to irradiate the first surface 202 of the second length L2 of the substrate 200.

In some configurations, the relofting system 302 may include one or more mirrors that reflect the portion 304aa of infrared radiation 304a of the infrared radiation 306a from the first radiation source 304a that travels through the first length L1 of the substrate 200 and away from the second surface 204 of the first length L1 of the substrate 200 back toward the second surface of 204 of the first length L1 of the substrate 200 to irradiate the second surface of 204 of the first length L1 of the substrate 200. Similarly, the relofting system 302 may include one or more mirrors that reflect the portion 304bb of infrared radiation 304b from the second radiation source 304b that travels through the second length L2 of the substrate 200 and away from the second surface 204 of the second length L2 of the substrate 200 back toward the second surface of 204 of the second length L2 of the substrate 200 to irradiate the second surface of 204 of the second length L2 of the substrate 200. Such mirrors may be adapted to move so as not to interfere with the movement of the movable axis 316.

As previously mentioned, the movable axis 316 may be movable from the second position to the first position to place the substrate 200 in position so as to be isolated from the radiation sources 304, such as during assembly line shut down operations. The movable axis 316 may be configured to move in a direction B from the second position shown in FIG. 4 to the first position shown in FIG. 3. In some configurations, such movement from the second position to the first position may occur as the substrate advancement speed is decelerating and/or the substrate advancement is stopped and while the radiation source continues to output energy. Movement of the movable axis 316 from the second position to the first position may operate to remove the first surface 202 of the substrate 200 from the facing relationship with the radiation sources 304.

Figure 6:
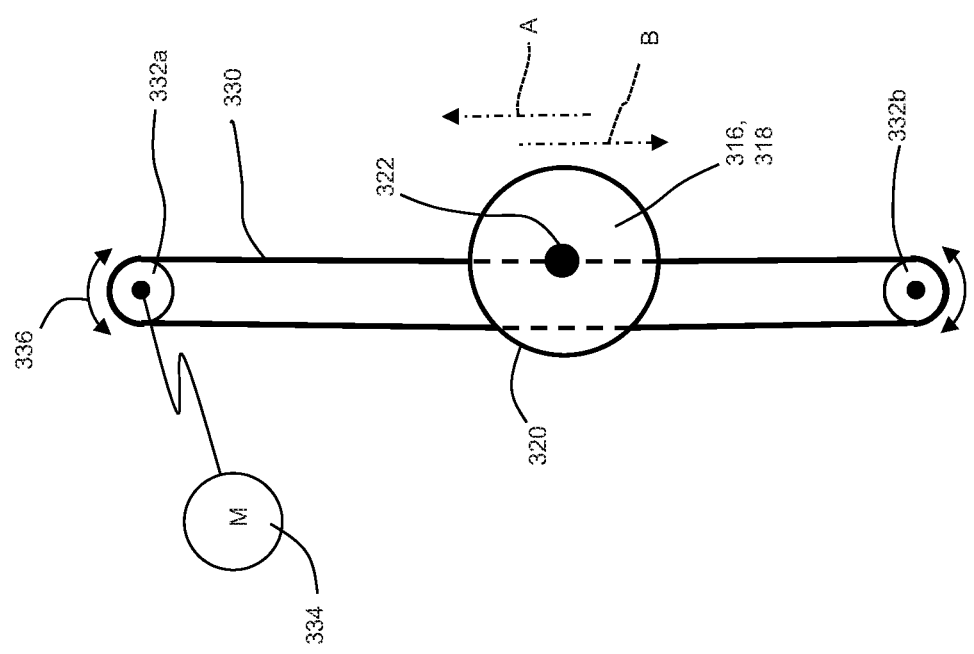
FIG. 6 is a schematic side view of a motor, belt, and pulley apparatus adapted to move the movable axis.

It is to be appreciated that the relofting system 302 may be configured in various ways to move the movable axis 316 between the first and second positions. For example, as shown in FIG. 6, the movable axis 316, which may be configured as a traversing idler 318, may be connected with a belt 330 that may be wrapped around pulleys 332a, 332b. In addition, a motor 334 may be connected with a pulley 332a to rotate the pulley 332a in clockwise and counterclockwise directions as indicated by bidirectional arrow 336. Thus, as the motor 334 rotates the pulley 332a, the belt 330 cause the movable axis 316 to move in direction A or direction B. The motor 334 may be configured as a servo motor. In some configurations, the motor 334 may be operatively connected with an accumulator 308, such as described above with reference to FIG. 2, so that the movement of the movable axis 316 may be coordinated with the accumulator 308 to help maintain desired speeds and/or tension of the substrate 200 during operation. It is to be appreciated that accumulator devices may be positioned upstream and/or downstream of the movable axis 316.

Figure 7:
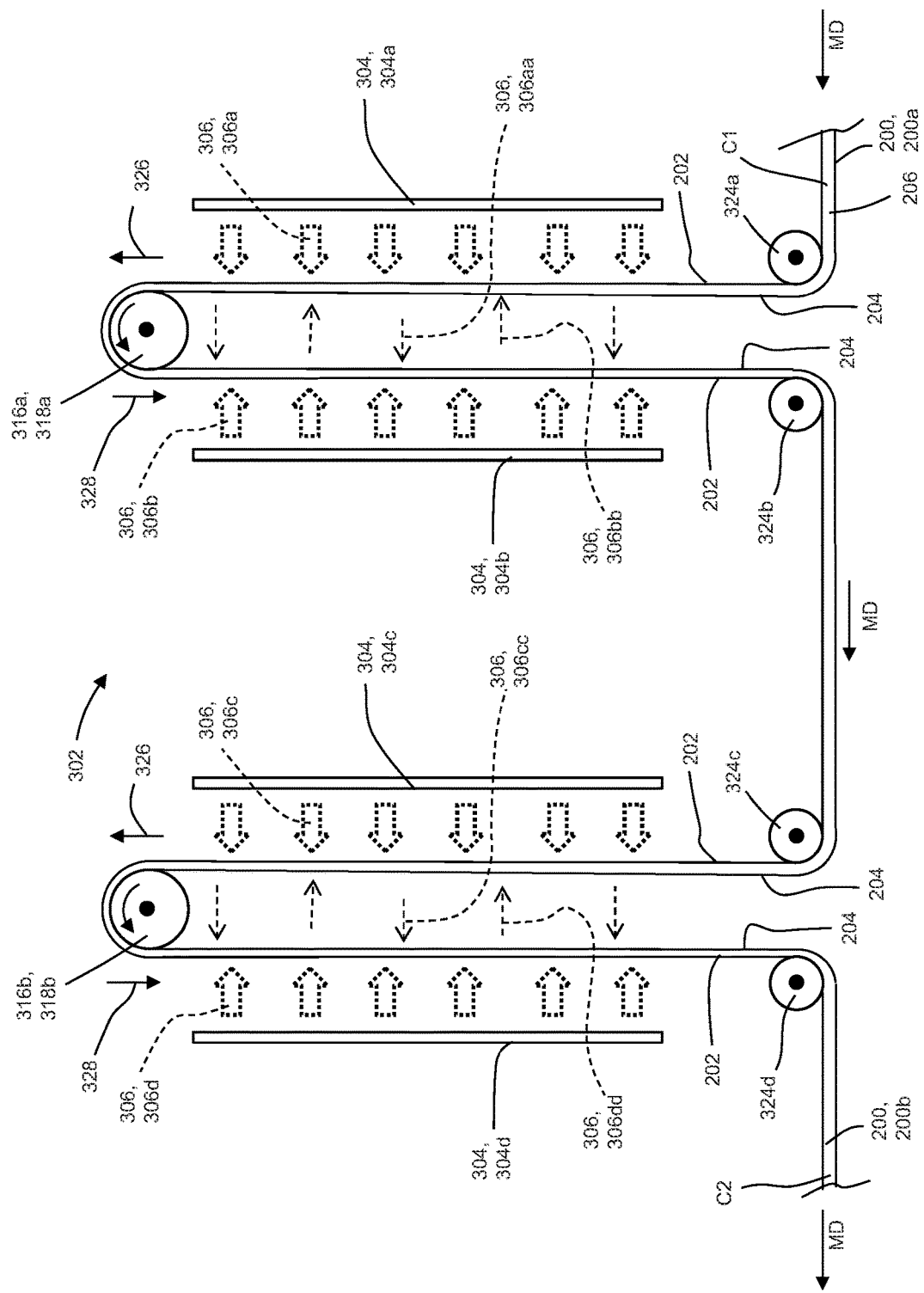
FIG. 7 is a schematic side view of a second system for relofting an advancing substrate.

It is to be appreciated that the relofting system 302 may be configured in other various ways. In some configurations, the relofting system 302 may include additional radiation sources 304 and movable axes 316. For example, as shown in FIG. 7, the relofting system 302 may include a first radiation source 304a and a second radiation source 304b, and a first movable axis 316a configured as a first traversing idler 318a. As discussed above, the first movable axis 316a may be movable between a first position and a second position to place the substrate 200 in facing relationship with (or isolate the substrate 200 from) the first and second radiation sources 304a, 304b. With continued reference to FIG. 7, the relofting system 302 may also include a third radiation source 304c and a fourth radiation source 304d, and a second movable axis 316b configured as a second traversing idler 318b. As such, the second movable axis 316b may be movable between a first position and a second position to place the substrate 200 in facing relationship with (or isolate the substrate 200 from) the third and fourth radiation sources 304c, 304d. In operation, the first and second radiation sources 304a, 304b may irradiate the advancing substrate 200 with infrared radiation 306a, 306b to heat and reloft the substrate 200. Infrared radiation 306aa, 306bb that may travel through the substrate 200 may also be used to heat and reloft the substrate 200, as discussed above. From the first and second radiation sources 304a, 304b, the substrate 200 advance to a third guide roller 324c and the second traversing idler 318b that direct the substrate 200 to advance past the third and fourth radiation sources 304c, 304d. The third and fourth radiation sources 304c, 304d may irradiate the advancing substrate 200 with infrared radiation 306c, 306d to further heat and reloft the substrate 200. Infrared radiation 306cc, 306dd that may travel through the substrate 200 may also be used to further heat and reloft the substrate 200 to the second caliper C2 greater than the first caliper C1. The substrate 200 may then advance from a fourth guide roller 324d that may direct the substrate 200 to other downstream converting and/or assembly operations. It is to be appreciated that the relofting system 302 may include more or less guide rollers than depicted in FIG. 7.

As previously mentioned, absorbent articles may be assembled with various components that may be relofted off-line, before assembly, or on-line, as part of the assembly process. Thus, the relofting system 302 may be included as a component or unit operation of an absorbent article assembly line 300. It is also to be appreciated that various components of the relofting system 302, such as radiation sources 304, may be positioned within an enclosure to help isolate adjacent equipment and/or operating personnel from infrared radiation and/or heat associated therewith. Such enclosures may be configured with cooling systems and/or fire suppression systems. It is also to be appreciated that the relofting system 302 may include other features. For example, the radiation sources 304 may include reflective shutters that open and close that expose or isolate the substrate 200 from infrared radiation 306. In some configurations, the relofting system 302 may utilize air or other fluids to help cool the relofted substrate 200b and/or the radiation sources 304. In addition, the speed and/or tension of the advancing substrate 200 may be adjusted before, during, and/or after being heated.

Peak Absorbance Wavelength Test Method

The peak absorbance wavelength of a test specimen is determined by measuring infrared transmittance and reflectance using an FT-IR spectrometer equipped with a mid-infrared integrating sphere that enables total hemispherical diffuse reflectance and diffuse transmittance measurements. A suitable bench-top system includes the Frontier IR Single Range Spectrometer (available from PerkinElmer Ltd, Bucks UK) equipped with a Mid-IR IntegratIR integrating sphere with an upward-looking configuration (available from Pike Technologies, Madison, Wis., USA) and a light trap (LTRP-01BG available from Avian Technologies, LLC, Sunapee, N.H.). The measurement system has a minimum resolution of 0.4 cm$^{-1}$, a spectral range of at least 5000-250 cm$^{-1}$, the integrating sphere has a 12 degree angle of incidence and a DTGS detector is used. A diffuse gold reference specific for upward-looking integrating spheres (also available from Pike Technologies) is used for collecting background spectrum. The measurement system is calibrated and operated as per the manufacturers' instructions, and all measurements are performed in a laboratory maintained at 23° C.±2° C. and 50%±2% relative humidity.

Obtain a test specimen by removing it from an absorbent article, if necessary. When excising the test specimen from an absorbent article, use care to not impart any contamination or distortion to the test specimen layer during the process. Test specimens should be cut to a size of 38 mm×38 mm. Test specimens are conditioned at 23° C.±2° C. and 50%±2% relative humidity for 2 hours prior to testing.

To measure the diffuse transmittance and diffuse reflectance of the test specimen, the measurement system is set up as follows. Set the wavelength range to 5000-400 cm$^{-1}$ and select an appropriate scan speed for the DTGS detector and FTIR instrument being used. For the Frontier FTIR instrument, an example scan speed is 0.2 cm/sec. The resolution is set to 4 cm$^{-1}$ with an appropriately corresponding J-stop. Set the scan time to 30-60 seconds. The flipper mirror on the integrating sphere is positioned such that it directs the beam toward the sample (reference standard as well as test specimen) at a 12 degree angle (known as "sample position"). A background spectrum is collected using the diffuse gold reference standard prior to analyzing the test specimen. For measuring reflectance, place the diffuse gold reference onto the sample port. Remove the transmission slide from the beam entrance port, which will provide access to the built-in slide mount. Collect a background spectrum. Replace the diffuse gold reference standard with the test specimen. Place light trap on top of the sample making sure that the receiving aperture of the light trap is aligned with the sample port. Collect the reflectance spectrum. For diffuse transmittance, place the diffuse gold reference onto the sample port. Remove the transmission slide from the beam entrance port, which will provide access to the built-in slide mount. Collect a background spectrum. Place the transmittance sample (test specimen) at the beam entrance port and collect the transmittance spectrum for the test specimen. The absorbance A(λ) of the test specimen is then calculated as A(λ)=1−(R $(\lambda)+T(\lambda))$, where $R(\lambda)$ is reflectance and $T(\lambda)$ is transmittance of the test specimen measured across the range of wavenumbers.

The Peak Absorbance Wavelength can be defined as the wavelength of any one of the absorbance peaks within the chosen wavelength range. The radiation sources 304 herein may be configured such that the wavelength of the infrared radiation 306 may about equal to the wavelength of the largest absorbance peak within the wavelength range, however this is provided as guidance and not a limitation.

The average absorbance can be calculated from the absorbance $A(\lambda)$ data collected according to Peak Absorbance Test Method. To calculate Average Absorbance, use the following formula:

$$A_{av} = \Sigma A(\lambda)_i E(\lambda)_i / \Sigma E(\lambda)_i$$

where summation is done for all data points within the chosen spectral range and $E(\lambda)$ is a spectral intensity function of the IR source. The spectral intensity function of the IR source can be calculated based on the formula for the spectral intensity radiation of the black body, otherwise known as Planck spectrum or Planck's law.

Caliper Test Method

The caliper of a test specimen is measured as the distance between a reference platform on which the specimen rests and a pressure foot that exerts a specified amount of pressure onto the specimen over a specified amount of time. All measurements are performed in a laboratory maintained at 23° C.±2° C. and 50%±2% relative humidity.

Caliper is measured with a universal micrometer, such as a Frank Type 16502 (available from Frank-PTI GMBH, Birkenau, Germany), or equivalent. The micrometer is equipped with a pressure foot capable of exerting a steady pressure of 0.5 kPa±0.01 kPa onto the test specimen with readings accurate to 0.001 mm. The pressure foot is a flat ground circular movable face with a diameter that is smaller than the test specimen and capable of exerting the required pressure. A suitable pressure foot has a diameter of 50 mm, however a smaller or larger foot can be used depending on the size of the specimen being measured. The test specimen is supported by a horizontal flat reference platform that is larger than and parallel to the surface of the pressure foot. The system is calibrated and operated per the manufacturer's instructions.

Obtain a test specimen by removing it from an absorbent article, if necessary. When excising the test specimen from an absorbent article, use care to not impart any contamination or distortion to the test specimen layer during the process. Test specimens are conditioned at 23° C.±2° C. and 50%±2% relative humidity for 2 hours prior to testing. To measure caliper, first zero the micrometer against the horizontal flat reference platform. Place the test specimen on the platform with the test location centered below the pressure foot. The pressure foot is lowered with a descent rate of 3.0 mm per second until the full pressure is exerted onto the test specimen. After a dwell time of 5 seconds, record the caliper of the test specimen to the nearest 0.01 mm. In like fashion, repeat for a total of five replicate test specimens. Calculate the arithmetic mean for Caliper and report to the nearest 0.01 mm.

Aspect Ratio Test Method

The aspect ratio of an aperture is the ratio of the major axis to the minor axis of the aperture (i.e. an intentional hole). These dimensions are measured using an optical microscope (Zeiss SV8 stereoscope, available from Zeiss Inc., New York, N.Y., or equivalent) equipped with a digital camera (Sony DKC-ST5, available from Sony Corp., Japan, or equivalent) that is interfaced to a computer running an image analysis software (MATLAB, available from The Mathworks Inc., Natick, Mass., or equivalent). All measurements are performed in a laboratory maintained at 23° C.±2° C. and 50%±2% relative humidity.

Obtain a test specimen by removing it from an absorbent article, if necessary. When excising the test specimen from an absorbent article, use care to not impart any contamination or distortion to the test specimen layer during the process. Test specimens are conditioned at 23° C.±2° C. and 50%±2% relative humidity for 2 hours prior to testing.

To measure the aperture dimensions, obtain an image of the test specimen that includes a calibrated distance scale, and open it in the image analysis software. The image resolution is calibrated using the calibrated distance scale to determine the number of pixels per millimeter. Now the dimensions of the apertures can be measured, excluding all partial apertures (those where the hole is not fully visible). Measure the major axis and minor axis for a given aperture and record each length to the nearest 0.01 mm. Divide the major axis length by the minor axis length and report as Aspect Ratio. In like fashion, repeat for at least 5 apertures. Calculate and report the arithmetic mean for Aspect Ratio.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A method for relofting a substrate, the method comprising:
advancing a substrate in a machine direction MD around a traversing idler having an axis, the substrate comprising a first surface and an opposing second surface and defining a width in a cross direction;
providing a first infrared radiation source;
directing a first length of the substrate to advance in a first direction; and moving the axis from a first position to a second position to place the first surface of the first length of the substrate in a facing relationship with the first infrared radiation source;

irradiating the first surface of the first length of the substrate with infrared radiation from the first infrared radiation source, wherein the substrate comprises a first caliper upstream of the first infrared radiation source and wherein the substrate comprises a second caliper downstream of the first infrared radiation source, wherein the second caliper is at least 1.2 times the first caliper;

redirecting a second length of the substrate around the axis to advance the second length of the substrate from the first direction to a second direction that is opposite the first direction, wherein the second surface of the first length of the substrate is in a facing relationship with the second surface of the second length of the substrate;

providing a second infrared radiation source in a facing relationship with the first surface of the second length of the substrate; and irradiating the first surface of the second length of the substrate with infrared radiation from the second infrared radiation source.

2. The method of claim 1, wherein the substrate comprises apertures, wherein the apertures comprise first aspect ratios upstream of the first infrared radiation source and wherein the apertures comprise second aspect ratios downstream of the first infrared radiation source, wherein the second aspect ratios are greater than the first aspect ratios.

3. The method of claim 1, wherein a portion of the infrared radiation from the first infrared radiation source travels through the first length of the substrate and away from the second surface of the substrate and irradiates the second surface of the second length of the substrate.

4. The method of claim 3, wherein a portion of the infrared radiation from the second infrared radiation source travels through the second length of the substrate and away from the second surface of the substrate and irradiates the second surface of the first length of the substrate.

5. The method of claim 1, wherein the substrate comprises a nonwoven.

6. The method of claim 5, wherein the nonwoven comprises bi-component fibers.

7. The method of claim 6, wherein the nonwoven comprises through air bonded bi-component fibers.

8. The method of claim 6, wherein the bi-component fibers comprise polyethylene terephthalate.

9. The method of claim 1, wherein the substrate comprises a peak absorbance wavelength and wherein the infrared radiation from the first infrared radiation source comprises a wavelength that is about equal to the peak absorbance wavelength.

10. A method for irradiating a substrate, the method comprising:

advancing a substrate in a machine direction MD, the substrate comprising a first surface and an opposing second surface and defining a width in a cross direction;

directing the substrate to advance in a first direction;

redirecting the substrate around a traversing idler having an axis to advance the substrate in a second direction, wherein the second direction is different than the first direction;

moving the axis from a first position to a second position to place the first surface of a first length of the substrate in a facing relationship with a first infrared radiation source; and irradiating the first surface of the first length of the substrate with infrared radiation from the first infrared radiation source.

11. The method of claim 10, wherein moving the axis from a first position to a second position further comprises placing the second surface of the substrate in a facing relationship with the second surface of the substrate.

12. The method of claim 10, wherein the first direction is opposite the second direction.

13. The method of claim 10, wherein moving the axis from the first position to the second position further comprises moving the axis in the first direction.

14. The method of claim 10, wherein moving the first axis from the first position to the second position further comprises placing the first surface of a second length of the substrate advancing in the second direction in a facing relationship with a second infrared radiation source; and irradiating the first surface of the second length of the substrate with infrared radiation from the second infrared radiation source.

15. The method of claim 14, wherein a portion of the infrared radiation from the first infrared radiation source travels through the first length of the substrate and away from the second surface of the substrate and irradiates the second surface of the second length of the substrate.

16. The method of claim 15, wherein a portion of the infrared radiation from the second infrared radiation source travels through the second length of the substrate and away from the second surface of the substrate and irradiates the second surface of the first length of the substrate.

17. The method of claim 10, further comprising moving the first axis from the second position to the first position to remove the first surface of the first length of the substrate from the facing relationship with the first infrared radiation source.

18. The method of claim 17, wherein the substrate decelerates from a first speed to a second speed, as the axis is moved from the second position to the first position.

19. The method of claim 10, wherein the substrate comprises a nonwoven.

20. The method of claim 19, wherein the nonwoven comprises through air bonded bi-component fibers.

21. The method of claim 10, wherein the substrate comprises a first caliper upstream of the first infrared radiation source and wherein the substrate comprises a second caliper downstream of the first infrared radiation source, wherein the second caliper is at least 1.2 times the first caliper.

22. The method of claim 10, wherein the substrate comprises apertures, wherein the apertures comprise first aspect ratios upstream of the first infrared radiation source and wherein the apertures comprise second aspect ratios downstream of the first infrared radiation source, wherein the second aspect ratios are greater than the first aspect ratios.

23. The method of claim 10, wherein the substrate comprises a peak absorbance wavelength and wherein the infrared radiation from the first infrared radiation source comprises a wavelength that is about equal to the peak absorbance wavelength.

24. The method of claim 10, further comprising:

combining the substrate with additional substrates and components to assemble a continuous length of absorbent articles; and separating the continuous length of absorbent articles into discrete absorbent articles.

25. The method of claim 24, wherein the substrate comprises a topsheet, and the additional substrates and components are selected from the group consisting of: backsheets, secondary topsheets, and absorbent cores.

\* \* \* \* \*